United States Patent
Ohashi et al.

(10) Patent No.: US 7,463,994 B2
(45) Date of Patent: Dec. 9, 2008

(54) METHOD AND DEVICE FOR DETECTING SURFACE STATE OF WORK PIECE

(75) Inventors: Kazuhito Ohashi, Okayama (JP); Shinya Tsukamoto, Okayama (JP)

(73) Assignee: Okayama University, Okayama (JP)

( * ) Notice: Subject to any disclaimer, the term of this patent is extended or adjusted under 35 U.S.C. 154(b) by 0 days.

(21) Appl. No.: 11/661,969

(22) PCT Filed: Sep. 9, 2005

(86) PCT No.: PCT/JP2005/017089

§ 371 (c)(1),
(2), (4) Date: Mar. 12, 2007

(87) PCT Pub. No.: WO2006/028295

PCT Pub. Date: Mar. 16, 2006

(65) Prior Publication Data

US 2007/0250275 A1    Oct. 25, 2007

(30) Foreign Application Priority Data

Sep. 10, 2004  (JP)  ............................. 2004-298203

(51) Int. Cl.
*G01K 17/00* (2006.01)
*G06F 15/00* (2006.01)

(52) U.S. Cl. .......................... 702/136; 702/33; 702/34; 702/133; 702/168; 374/179

(58) Field of Classification Search .................. 702/33, 702/34, 41, 42, 57, 81–84, 130, 136, 167–168; 73/104–105; 374/179–182; 33/448

See application file for complete search history.

(56) References Cited

U.S. PATENT DOCUMENTS 2,048,681 A * 7/1936 Davidson et al. ............ 136/232

(Continued)

FOREIGN PATENT DOCUMENTS

JP    A 02-254617    10/1990

(Continued)

OTHER PUBLICATIONS

Vujevic, Dusan, Transient Thermoelectromotive Forces on Binding Posts, Feb. 1996, IEEE Transactions on Instrumentation and Measurement, vol. 45, No. 1, pp. 341-344.*

(Continued)

*Primary Examiner*—Eliseo Ramos Feliciano
*Assistant Examiner*—Mi'schita' Henson
(74) *Attorney, Agent, or Firm*—Oliff & Berridge, PLC

(57) ABSTRACT

A work piece 1 mounted on a movable table 22 is rotated while adjusting cutting depths of a grinding wheel 23 by means of feed motor so as to perform cylindrical grinding. During the cylindrical grinding, a thermocouple 42 is pushed to and caused to contact the rotating cylindrical grinding surface 1*a* of the work piece 1 at a constant pressure and thermoelectromotive force generated by the thermocouple 42 is measured. Surface roughness data corresponding to the measured thermoelectromotive force are obtained on the basis of the thermoelectromotive data obtained by the measurement and correlation between thermoelectromotive force and surface roughness concerning a known standard surface previously obtained and memorized. The surface roughness data are output and displayed on a display section. Therefore, an in-process measurement of surface state of the work piece 1 can be performed, while the machining such as cylindrical grinding is being carried out.

41 Claims, 22 Drawing Sheets

U.S. PATENT DOCUMENTS

| | | | | |
|---|---|---|---|---|
| 2,696,118 A | * | 12/1954 | Petry | 374/182 |
| 5,727,915 A | * | 3/1998 | Suzuki | 414/1 |
| 5,791,782 A | * | 8/1998 | Wooten et al. | 374/208 |
| 5,929,438 A | | 7/1999 | Suzuki et al. | |
| 2006/0075760 A1 | * | 4/2006 | Im et al. | 62/3.7 |

FOREIGN PATENT DOCUMENTS

| | | |
|---|---|---|
| JP | A 05-177512 | 7/1993 |
| JP | A 06-099336 | 4/1994 |
| JP | A 06-258060 | 9/1994 |
| JP | A 09-196940 | 7/1997 |
| JP | A 10-138095 | 5/1998 |
| JP | A 11-148812 | 6/1999 |
| JP | A 2001-004455 | 1/2001 |
| JP | A 2002-340518 | 11/2002 |
| JP | A 2003-130606 | 5/2003 |

OTHER PUBLICATIONS

Kashihara, et al; (2005); "In-process Measurement of Surface Roughness in Grinding Process (1$^{st}$ Report)-Principle of Measuring Surface Roughness-"; The Japan Society for Precision Engineering; pp. 861-862.

* cited by examiner (A)

(B)

(A)

(B)

(A)

(B)

METHOD AND DEVICE FOR DETECTING SURFACE STATE OF WORK PIECE

TECHNICAL FIELD

This invention relates to a method for detecting surface state of a work piece and a device for detecting surface state of the work piece for carrying out the method in order to detect a surface roughness and/or surface temperature variation of the surface of the work piece subjected to a surface working (machining such as cutting, grinding or the like) or a surface processing (physical or chemical processing such as rolling, skin pass rolling, coating or the like), and more particularly to a method and a device being capable of favorably detecting surface state of a work piece made of an electrically conductive material such as a metal or the like by an in-process or post-process measurement.

BACKGROUND ART

In order to measure the surface roughness, heretofore, various methods have been used. For example, according to a stylus method, a stylus is brought into contact with a surface to be measured and moved on the surface, while according to a non-stylus or non-contact method, laser light or the like is focused to illuminate a surface to be measured and then the surface is scanned by the focused laser light to detect its reflected light. In either method, a sectional shape of the surface to be measured is obtained and a surface roughness is determined on the basis of the obtained sectional shape.

By the way, in order to measure the surface roughness of a work piece worked by a machine tool such as a machining center or a lathe, after the working on the machine tool has been temporarily stopped, the measurement is conducted while the work piece is removed from the machine tool and set on a surface roughness tester, or while the work piece is still mounted on the machine tool. Even with measurement of the non-stylus system, the surface roughness could not be measured in a real time manner under the circumstances using a machining liquid or cutting oil. With the measuring methods of the prior art, accordingly, it is difficult or even impossible to detect surface roughness in a real time manner during working of a work piece. Consequently, the machining has to be interrupted for the measuring process of the roughness, which has been an important reason for impeding improvement in production efficiency and product quality.

In order to improve the working accuracy and quality more efficiently, therefore, it has become an important task to establish the technique for clarifying surface roughness of an object to be measured (work piece) in a dynamic condition where the work piece is still being driven or worked, in other words, an in-process measurement has been required. Namely, if the measurement of surface roughness is carried out in-process manner, it becomes possible to monitor the accuracy of the surface being cut so that increase of unmanned machine tools and smooth automatic operation without troubles can be progressed, thereby greatly contributing to improvement in production efficiency and product quality.

Even in the case of post-process measurement of the surface roughness, moreover, there is a following problem. If a narrow portion with a physical limitation such as a fine aperture impossible to insert a stylus in the stylus method, or impossible to detect reflected light in the optical method, the object has to be cut to expose the portion to be measured before the roughness is actually measured. Accordingly, it has been an important theme to establish a technique being capable of efficiently measuring the surface roughness of the narrow portion without cutting or breaking down the object to be measured.

Main methods for measuring the surface roughness of the prior art are shown in the following patent documents 1 to 7. These are classified by measuring principles into methods based on properties of work pieces (patent documents 1 and 3), optical measuring methods (patent documents 2, 5 and 7), method utilizing styluses (patent document 4) and method using ultrasonic waves (patent document 6).

Patent document 1: Japanese Patent Application Opened No. 2003-130,606
Patent document 2: Japanese Patent Application Opened No. H11-148,812 (1999)
Patent document 3: Japanese Patent Application Opened No. 2002-340,518 (2002)
Patent document 4: Japanese Patent Application Opened No. H10-138,095 (1998)
Patent document 5: Japanese Patent Application Opened No. H6-258,060 (1994)
Patent document 6: Japanese Patent Application Opened No. H5-177,512 (1993)
Patent document 7: Japanese Patent Application Opened No. H6-99,336 (1994)

DISCLOSURE OF THE INVENTION

Problem to be Solved by the Invention

The methods for measuring surface roughness disclosed in the above patent documents 1 to 7 include the following tasks from the standpoint of possibility of the in-process measurement.

The patent document 1, Japanese Patent Application Opened No. 2003-130,606 has disclosed a method for measuring surface roughness of recording surface of magnetic tape in which the surface roughness is obtained from thermal asperity waveforms when the surface to be measured is in contact with and sliding on a magnetic head in order that measurement can be performed with a sensitivity similar to that received by the magnetic head actually upon contacting of the magnetic tape with the magnetic head. With this method, however, since the magnetic head is used, objects to be measured are limited to magnetic substances and this method suffers from a problem that this method is not applicable to metals other than magnetic substances. Moreover, by using the magnetic head, roughness sensors including the magnetic head are complicated. Further, as the region where the magnetic head contacts is required to be comparatively wide, this method is not suitable for roughness measurement at a small area. Furthermore, as the magnetic head could not tolerate the abrasion caused by the wide mating magnetic tape surface, this method is difficult to apply even to a measurement of the order of a few microns.

The patent document 2, Japanese Patent Application Opened No. H11-148,812 (1999) has disclosed a method for measuring surface roughness of an epitaxial growth layer formed on a substrate for forming a vertical bipolar transistor, in which the surface of the epitaxial growth layer is illuminated by ultraviolet light of short wavelengths so that the amount of its reflected light is measured by a ultraviolet spectrometer to obtain the surface roughness. However, as there is need in this method for the object to be measured to be stationary for using the ultraviolet spectrometer so that this method is not suitable for in-process measurement. Further, a problem that the construction of the measuring system is complicated remains to be solved.

The patent document 3, Japanese Patent Application Opened No. S57-30,308 (1982) has disclosed a method for measuring surface roughness of a sheet-shaped object to be measured such as a magnetic tape, in which the air interposed between a standard surface and the object to be measured is sucked so that the surface roughness is judged on the basis of the adhering time between the standard surface and the object. In this method, however, as the object must be arranged under a stationary condition, this method is not suitable for in-process measurement. Moreover, the construction of measuring system becomes complicated because of the need for preparing a vacuum pump for sucking the air and a desiccator for an airtight room.

The patent document 4, Japanese Patent Application Opened No. H10-138,095 (1998) has disclosed a method for measuring dimensions and surface roughness of a work piece at a time by means of a dimension measuring device using a surface roughness probe of a stylus type. With this method, the surface roughness can be measured while the work piece is being worked, however, as the principle of surface roughness measurement is a stylus method, if the tracing speed (measuring speed) is increased, the stylus could not accurately follow the shape of the surface to be measured so that this method has an disadvantage that the surface roughness can only be performed within a range of comparatively low speed. Therefore, this method cannot be applied to in-process surface roughness measurement when the object to be measured is moved at a high speed as in usual machining processes, and the construction of the measuring system itself for the surface roughness sensor including a stylus becomes complicated to provide a further problem. In the case of a stylus type, moreover, the method suffers a disadvantage from a limitation of measuring environmental condition such as that the measured surface must be substantially in a horizontal position. Even with the non-contact system such as optical system or the like, not limited to the contact system such as stylus type, in order to perform the in-process measurement, the relative movement between the surface to be measured and the measuring sensor (probe or detector) must be linear or rotary movement with high accuracy. In any measuring system, it will be impossible to effect the surface roughness measurement or measuring accuracy is considerably lowered if the movements of the measured object and measuring sensor include irregular components.

The patent document 5, Japanese Patent Application Opened No. H6-258,060 (1994) has disclosed a non-contact surface roughness measuring method using an ellipsometer. The ellipsometer is a precise measuring device for thin films, utilizing variations in polarized condition of reflected lights when polarized light illuminates a boundary surface of an object by the ellipsometer. In the method disclosed in the patent document 5, when laser light illuminates a surface to be measured, refractive index and absorption coefficient are measured by the use of the ellipsometer to obtain the surface roughness. With this optical system using laser light, although the measuring speed can be increased in comparison with the stylus type, the optical measurement system would be subject to optical influence by optical disturbances such as optical atmosphere, for example, optical affection of mercury lamps, sodium lamps or the like arranged in a factory because of the optical non-contact measurement. In order to carry out this method, therefore, any approach is required for maintaining measuring circumstances being free from disturbances. In the case that water, oil and the like are attached to the surface to be measured, or cutting oil or the like is splashed during cutting operation, normal reflected light becomes difficult to be obtained, so that tedious task is required to clean for degreasing the surface or to prevent splashing of the oil, which would disturb the measurement desired to be simply performed.

The patent document 6, Japanese Patent Application Opened No. H5-177,5125 (1993) has disclosed a method for measuring surface roughness in which ultrasonic waves are applied to a portion being cut through a liquid medium during cutting, and reflected waves from the surface are detected so as to detect the surface roughness. With this method, although the measurement of surface roughness of the surface being cut can be performed, the measuring circumstances being free from disturbance are required because the roughness measuring region must be in a liquid atmosphere so that the roughness measurement cannot be simply performed as is also the case with the invention disclosed in the patent document 5.

The patent document 7, Japanese Patent Application Opened No. H6-99,336 (1994) has disclosed a method for measuring surface roughness of a work piece on a machine tool without being removed therefrom by means of a small type optical surface roughness meter mounted on the horizontal lathe. Insofar as a surface roughness meter of the prior art is used, the measurement of the surface roughness must be carried out only after the working has been stopped so that there is a problem that the in-process measurement during working could not be effected.

Accordingly, it is an object of the invention to provide a method for detecting surface state of a work piece and a device for detecting surface state of the work piece for favorably carrying out the method, which are applicable to a wide variety of objects to be measured, particularly to whole electrically conductive materials and can detect surface roughness and/or surface temperature variation of an in-process work piece without being affected by disturbances under any dynamic conditions, and which further can accurately and simply detect surface roughness and/or surface temperature variation of objects still mounted on a machine without requiring particular treatment, whose surfaces would be impossible or difficult to be measured by the methods of prior art without being treated by cutting or the like.

Means for Solving Problem

In order to achieve the object of the invention described above, the inventors of the present application have been devoting ourselves to investigation, and found an effective solution as a result, thereby accomplishing the present invention. In the course of our investigation, first we have noticed a shift phenomenon that thermoelectromotive forces do not coincide with each other before and after grinding a work piece when surface temperatures are measured by the use of contact-type thermocouples in experiments of traverse grinding of cylindrical surfaces carried out in the development research process. In the second place, while we have been studying the reason, we have found that the reason for the occurrence of the shift phenomenon lies in the fact that the surface roughness of the work piece are greatly different from each other before and after the grinding. Moreover, we, inventors have thought that the frictional heat generated upon the thermocouple contacting the rotating work piece exhibits different values before and after grinding owing to difference in surface roughness, or in other words, the surface temperatures of the work piece do not coincide with each other before and after grinding owing to difference in thermoelectromotive force detected by the thermocouple. We have therefore assumed that there is any relation between the surface roughness of the work piece and the frictional heat. In order to prove this assumption, we have performed the following experiments and the like, from the results of which we have arrived at the original idea of the in-process surface roughness sensor and accomplish the surface roughness measuring principle of the present inventions based on the thermoelectromotive force of thermocouple. The surface roughness measuring principle is based upon the fact that when thermocouple probes consisting of a plurality of different metallic materials under a non-contact condition are brought into contact with a surface to be measured of an electrically conductive object and caused to do a relative movement with respect to the surface to be measured, there is the correlation between the surface roughness of the surface to be measured and the thermoelectromotive force generated upon the contact and the relative movement therebetween. The present invention performs the surface roughness measurement on the basis of the fact that the existence of the correlation and utilizing the correlation.

As a first evidence, variance in thermoelectromotive force caused by the surface roughness has been examined. As the result, we found that as the surface roughness of a work piece becomes greater, the detected thermoelectromotive force also becomes greater and they are in linear relationship. Then, we carried out experiments for studying the surface roughness of work pieces and variations in thermoelectromotive force caused by variations in circumferential speed of the work pieces. As the result, we found that the greater the circumferential velocity of the work pieces, the greater is frictional heat and hence the greater the detected thermoelectromotive force. On the recognition of these results of the experiments, we succeeded in clarification of the surface roughness measurement principle described above. In addition, the thermoelectromotive force $\Delta E$ measured by a thermocouple is represented by the following formula (1) on the basis of the principle. Namely, as the thermoelectromotive force measured by the thermocouple includes not only the heat corresponding to the surface temperature but also the frictional heat produced by the contact between the thermocouple and the surface to be measured, this state is represented as the following formula.

$$\Delta E = \alpha \cdot \Delta T + \beta \cdot Ry \quad (1)$$

In this case, $\alpha$ is a known value determined depending upon a used thermocouple and is an inherent value of the thermocouple (referred to hereafter as "temperature coefficient"), while $\Delta T$ is temperature variation of a surface to be measured. Further, $\beta$ is a coefficient (referred to hereinafter as "roughness coefficient") induced by a relation between the thermoelectromotive force and surface roughness depending upon the contact condition of the thermocouple (contact length of the thermocouple with the surface to be measured, contact pressure, and the like) and the relative movement condition (relative speed of the thermocouple at the contact point with respect to the surface to be measured, and the like). The roughness coefficient $\beta$ is varied by the temperatures of the surface to be measured and the frictional heat caused by the contact between the thermocouple and the surface to be measured. Finally, Ry is roughness of the surface to be measured.

The present invention has been achieved based on the recognition that there is the relation as the formula (1) between the thermoelectromotive force measured by the thermocouple, the surface roughness and the surface temperature, and the invention provides the following surface state detecting method for a work piece and the surface state detecting device for carrying out the method.

More specifically, first, the invention proposes a method for detecting surface state of a work piece characterized in that a measuring thermocouple in contact with a surface to be measured of the work piece is caused to perform a relative movement with respect to the surface to be measured so that generated thermoelectromotive force of the measuring thermocouple is measured, and a surface roughness and/or a surface temperature variation of the surface to be measured is obtained from the measured thermoelectromotive force on the basis of correlation data between thermoelectromotive forces, surface roughness and/or surface temperature variations previously obtained by bringing a data collecting thermocouple the same as or the same kind as the measuring thermocouple into contact with a standard surface whose surface roughness and/or surface temperature has been known and by causing the data collecting thermocouple to perform a relative movement with respect to the standard surface under the same contact condition and the same relative movement condition as those of the measuring thermocouple with respect to the surface to be measured. There are two cases for collecting the correlation data. First, the data are obtained by the use of a measuring thermocouple (a case using a data collecting thermocouple the same as the measuring thermocouple), and second, the data are obtained by the use of a data collecting thermocouple the same kind as the measuring thermocouple (the data collecting thermocouple having the temperature coefficient $\alpha$ the same as the temperature coefficient of the measuring thermocouple). In the former case, the surface state detecting device later described according to the invention can be used as a data collecting device, and in the latter case, a data collecting device is used, which has the construction the same as the surface state detecting device. However, the former may be preferably employed from the view point of the practical use.

In such a preferable configuration carrying out the method, first and second measuring thermocouples are used as the measuring thermocouples, and the first correlation data are previously obtained by a first data collecting thermocouple the same as or the same kind as the first measuring thermocouple, while the second correlation data are previously obtained by a second data collecting thermocouple the same as or the same kind as the second measuring thermocouple. These correlation data are represented by the formula (1), and the first correlation data are represented by $\Delta E = \alpha 1 \cdot \Delta T + \beta 1 \cdot Ry$, while the second correlation data are represented by $\Delta E = \alpha 2 \cdot \Delta T + \beta 2 \cdot Ry$. In these formulas, $\alpha 1$ is the temperature coefficient inherent in the first data collecting thermocouple 1 (and the first measuring thermocouple), and $\alpha 2$ is the temperature coefficient inherent in the second data collecting thermocouple (and the second measuring thermocouple). Moreover, $\beta 1$ is the roughness coefficient induced from the relation between the thermoelectromotive force and the surface roughness depending upon the contact condition and relative movement condition of the first data collection thermocouple with respect to a standard surface (the same as the contact condition and relative movement condition of the first measuring thermocouple with respect to the surface to be measured), and $\beta 2$ is the roughness coefficient induced from the relation between the thermoelectromotive force and the surface roughness depending upon the contact condition and relative movement condition of the second data collecting thermocouple with respect to the standard surface (the same as the contact condition and relative movement condition of the second measuring thermocouple with respect to the surface to be measured).

And, the thermoelectromotive force is measured by the first and second measuring thermocouples, the surface roughness Ry of the surface to be measured and/or the surface temperature variation $\Delta T$ is obtained from the thermoelectromotive force $\Delta E1$ measured by the first measuring thermocouple and the thermoelectromotive force $\Delta E2$ measured by the second measuring thermocouple on the basis of the correlation data. Namely, the surface roughness Ry is obtained as $Ry=(\alpha2\cdot\Delta E1-\alpha1\cdot\Delta E2)/(\alpha2\cdot\beta1-\alpha1\cdot\beta2)$ by eliminating $\Delta T$ (canceling the output arising from the temperature changes) from the correlation formula $\Delta E1=\alpha1\cdot\Delta T+\beta1\cdot Ry$ concerning the thermoelectromotive force $\Delta E1$ obtained by the first correlation data and from the correlation formula $\Delta E2=\alpha2\cdot\Delta T+\beta2\cdot Ry$ concerning the thermoelectromotive force $\Delta E2$ obtained by the second correlation data. On the other hand, the surface temperature variation $\Delta T$ is obtained as $\Delta T=(\beta2\cdot\Delta E1-\beta1\cdot\Delta E2)/(\alpha1\cdot\beta2-\alpha2\cdot\beta1)$ by eliminating Ry (canceling the output arising from the surface roughness) from the both the correlation data. In this case, if the first and second measuring thermocouples (first and second data collecting thermocouples) are of the same kind, $\alpha1$ is equal to $\alpha2$ ($\alpha1=\alpha2$), and hence $\Delta E1=\alpha1\cdot\Delta T+\beta1\cdot Ry$ and $\Delta E2=\alpha1\cdot\Delta T+\beta2\cdot Ry$ so that $Ry=(\Delta E1-\Delta E2)/(\beta1-\beta2)$ and $\Delta T=(\beta2\cdot\Delta E1-\beta1\cdot\Delta E2)/(\alpha1\cdot\beta2-\alpha2\cdot\beta1)$. Needless to say, moreover, in the case that the first and second measuring thermocouples are of the same kind as with this case, at least one of the contact condition and the relative movement condition (at the contact point with the surface to be measured) of each of the measuring thermocouples with respect to the surface to be measured must be different from each other. Probably, if the contact conditions and the relative movement conditions are the same, respectively, $\beta1$ becomes equal to $\beta2$ ($\beta1=\beta2$). In the case that the thermoelectromotive force $\Delta E1$ is measured by causing the first measuring thermocouple to do the relative movement under a condition producing a relative speed at a contact point with the surface to be measured and the thermoelectromotive force $\Delta E2$ is measured by causing the second measuring thermocouple to do the relative movement under a condition not producing a relative speed at a contact point with the surface to be measured, the thermoelectromotive force $\Delta E2$ measured by the second measuring thermocouple is generated only by the surface temperature of the surface to be measured because no frictional heat occurs by the contact between the second measuring thermocouple and the surface to be measured. Accordingly, although the first correlation data are obtained as $\Delta E=\alpha1\cdot\Delta T+\beta1\cdot Ry$, the second correlation data are obtained as $\Delta E=\alpha2\cdot\Delta T$ which does not have a term concerning Ry, and the temperature variation $\Delta T$ of the surface to be measured is obtained as $\Delta T=\Delta E2/\alpha2$ only from the correlation formula $\Delta E2=\alpha2\cdot\Delta T$ of the thermoelectromotive force E2 based upon the second correlation data. On the other hand, the surface roughness Ry is obtained as $Ry=(\alpha2\cdot\Delta E1-\alpha1\cdot\Delta E2)/(\alpha2\cdot\beta1)$ by eliminating $\Delta T$ from the correlation formula described above and the correlation formula $\Delta E=\alpha1\cdot\Delta T+\beta1\cdot Ry$ of the thermoelectromotive force E1 based on the first correlation data. In this case, when the first and second measuring thermocouples (the first and second data collecting thermocouples) are of the same kind, the surface roughness Ry is obtained as $Ry=(\Delta E1-\Delta E2)/\beta1$, because $\alpha1=\alpha2$ and hence $\Delta E1=\alpha1\cdot\Delta T+\beta1\cdot Ry$ and $\Delta E2=\alpha1\cdot\Delta T$.

In the case that there is dispersion or irregularity in the surface roughness and/or surface temperature and it is necessary to detect its distribution, this requirement can be fulfilled by a plurality of sets each consisting of first and second measuring thermocouples. The plurality of the sets of thermocouples are brought into contact with a surface to be measured at a plurality of locations so that the surface roughness and/or surface temperature at the plurality of locations on the surface to be measured are obtained at a time. In this case, the procedures for obtaining the surface roughness Ry and/or surface temperature variation $\Delta T$ by means of the first and second measuring thermocouples of each set can be performed in the same manner as those as described above.

In the case that the surface temperature of a surface to be measured is constant and its variation $\Delta T$ is zero or known, a plurality of measuring thermocouples (and data collecting thermocouples) as described above need not be used, and the surface roughness of the surface to be measured can be detected by the use of one measuring thermocouple (and one data collecting thermocouple). In this case, surface roughness $Ry=\Delta E/\beta$ is obtained from the thermoelectromotive force $\Delta E$ measured by the measuring thermocouple on the basis of the correlation data $\Delta E=\beta\cdot Ry$ not having a term concerning the surface temperature in the formula (1).

In such a case that only the surface roughness of a work piece will be detected, the following method can be employed when the surface temperature of the work piece is not known. Namely, a data collecting thermocouple in contact with a standard surface whose surface roughness and surface temperature have been known is caused to perform a relative movement with respect to the standard surface to generate thermoelectromotive force of the data collecting thermocouple so that correlation data between the generated thermoelectromotive force of the data collecting thermocouple and the surface roughness are previously obtained with surface temperature as a parameter, and surface temperature of a surface to be measured of the work piece is measured, and that a measuring thermocouple the same as or the same kind as the data collecting thermocouple is brought into contact with the surface to be measured and is caused to perform a relative movement with respect to the surface to be measured under the same contact condition and the same relative movement condition as those of the data collecting thermocouple with respect to the standard surface so as to generate thermoelectromotive force of the thermocouple, and the generated thermoelectromotive force is measured, from which measured thermoelectromotive force, surface roughness of the surface to be measured is obtained on the basis of the correlation data corresponding to the measured surface temperature. The surface temperature of the work piece can be measured by the use of a known non-contact thermometer such as an infrared thermometer.

In the second place, the invention proposes, as a device for carrying out the surface state detecting method, a device for detecting surface state of a work piece characterized in comprising measuring means for measuring thermoelectromotive force of a measuring thermocouple generated by causing the measuring thermocouple to perform a relative movement with respect to a surface to be measured of the work piece under a condition contacting the surface to be measured, a memory section for memorizing correlation data between thermoelectromotive forces, surface roughness and/or surface temperature variations previously obtained by bringing a data collecting thermocouple the same as or the same kind as the measuring thermocouple into contact with a standard surface whose surface roughness and/or surface temperature has been known and causing the data collecting thermocouple to perform a relative movement with respect to the standard surface under the same contact condition and the same relative movement condition as those of the measuring thermocouple with respect to the surface to be measured, an arithmetic section for calculating surface roughness and/or surface temperature variation of the surface to be measured from the thermoelectromotive force measured by the measuring means on the basis of the correlation data, and information output section for outputting information regarding the surface roughness and/or surface temperature variation of the surface to be measured calculated by the arithmetic section. It is noted that, as the memory section, arithmetic section and information output section, general control instruments may be used such as a personal computer, microcomputer or the like. For example, memories in these computers may be used as the memory section, and arithmetic output devices including a central processing unit may be used as the arithmetic section and the information output section. The information outputting by the information output section includes the outputting aspect such as displaying information concerning surface roughness and/or surface temperature variation of surface to be measured, and outputting data to other analyzer. In the case that distribution of surface roughness or surface temperature of a surface to be measured is detected using a plurality of sets of thermocouples, imaging of these distributions of the surface roughness and temperature can be performed.

In a preferable configuration of such a surface state detecting device, the measuring means is constructed to separately measure the thermoelectromotive force $\Delta E1$ generated by a first measuring thermocouple and the thermoelectromotive force $\Delta E2$ generated by a second measuring thermocouple, and the memory section is constructed to memorize first correlation data $\Delta E = \alpha 1 \cdot \Delta T + \beta 1 \cdot Ry$ obtained by the use of a first data collecting thermocouple the same as or the same kind as the first measuring thermocouple and second correlation data $\Delta E = \alpha 2 \cdot \Delta T + \beta 2 \cdot Ry$ obtained by the use of a second data collecting thermocouple the same as or the same kind as the second measuring thermocouple, while the arithmetic section is constructed to calculate the surface roughness of the surface to be measured $Ry = (\alpha 2 \cdot \Delta E1 - \alpha 1 \cdot \Delta E2)/(\alpha 2 \cdot \beta 1 - \alpha 1 \cdot \beta 2)$ and/or surface temperature variation $\Delta T = (\beta 2 \cdot \Delta E1 - \beta 1 \cdot \Delta E2)/(\alpha 1 \cdot \beta 2 - \alpha 2 \cdot \beta 1)$ on the basis of the first and second correlation data. Namely, the first and second measuring thermocouples are of the same kind having the same temperature coefficient $\alpha 1$, and the arithmetic section is adapted to calculate the surface roughness of the surface to be measured $Ry = (\Delta E1 - \Delta E2)/(\beta 1 - \beta 2)$ and/or the surface temperature variation $\Delta T = (\beta 2 \cdot \Delta E1 - \beta 1 \cdot \Delta E2)/(\alpha 1 \cdot \beta 2 - \alpha 1 \cdot \beta 1)$. Moreover, in the case that the measuring means is constructed to measure the thermoelectromotive force $\Delta E1$ by causing the first measuring thermocouple to perform a relative movement with respect to the surface to be measured under a contact condition producing a relative speed at the contact point of the first measuring thermocouple with the surface to be measured and to measure the thermoelectromotive force $\Delta E2$ by causing the second measuring thermocouple to perform a relative movement with respect to the surface to be measured under a contact condition not producing relative speed at the contact point of the second measuring thermocouple with the surface to be measured, the memory section is constructed to memorize the first correlation data $\Delta E = \alpha 1 \cdot \Delta T + \beta 1 \cdot Ry$ obtained using the first data collecting thermocouple and the second correlation data $\Delta E = \alpha 2 \cdot \Delta T$ obtained using the second data collecting thermocouple, and the arithmetic section is constructed to calculate the surface roughness of the surface to be measured $Ry = (\alpha 2 \cdot \Delta E1 - \alpha 1 \cdot \Delta E2)/(\alpha 2 \cdot \beta 1)$ and/or surface temperature variation $\Delta T = \Delta E2/\alpha 2$ from $\Delta E1 = \alpha 1 \cdot \Delta T + \beta 1 \cdot Ry$ and $\Delta E2 = \alpha 2 \cdot \Delta T$. Further, in the case that the first and second measuring thermocouples are of the same kind, the arithmetic section is constructed to calculate the surface roughness of the surface to be measured $Ry = (\Delta E1 - \Delta E2)/\beta 1$. Furthermore, in the case that the surface temperature of the surface to be measured is constant and the surface temperature variation $\Delta T$ is zero or already known, the surface roughness of the surface to be measured is detected using only one measuring thermocouple.

In the surface state detecting method or device, in the case that the surface to be measured has a conductivity, the measuring means is so constructed that the thermoelectromotive force is measured by bringing tips of first and second thermocouple wires (metals of different kinds as usual) constituting the measuring thermocouple into contact with the surface to be measured under a condition that the tips are spaced apart from each other. It is also possible that the tips of the first and second thermocouple wires are connected to each other by a wear resistant member so that the measuring means is constructed to measure the thermoelectromotive force by bringing the wear resistant member into contact with the surface to be measured. Moreover, in the case that the entire work piece including the surface to be measured is integrally formed from an electrically conductive material (for example, a metal), the measuring means is constructed to measure the thermoelectromotive force by bringing the tip of one of the first and second thermocouple wires constituting the measuring thermocouple into contact with the surface to be measured and connecting the tip of the other thermocouple wire to part of the work piece other than the surface to be measured. Further, the tip of at least one of the first and second thermocouple wires constituting the measuring thermocouple is constructed by a rotatable circular disk-shaped probe adapted to be in point contact with the surface to be measured. Namely, in the case that a work piece is integrally formed from an electrically conductive material, tips of both the thermocouples may be constructed by the probes, or one of tips is constructed by the probe, and the other tip is connected to a suitable portion of the work piece. In the case of a work piece of a non-conductive material, tips of both the thermocouples are formed by aforementioned probes. In the case that tips of both the thermocouples are formed by aforementioned probes in this manner, the measuring means is so constructed to have a circular disk-shaped probe which is forcedly rotated so as to produce a relative speed (in a manner to generate frictional heat) at a contact point with the surface to be measured. In the case that it is desired to employ correlation data in which the second term ($\beta \cdot Ry$) in the formula (1) is eliminated in a manner that frictional heat caused by contact of the surface to be measured is not generated, the measuring means is so constructed to have a circular disk-shaped probe which performs a free rotation so as not to produce any relative speed at a contact point with the surface to be measured. In other words, the probe is adapted to roll on the surface to be measured. Moreover, it is also possible that the tip of at least one of the first and second thermocouple wires constituting the measuring thermocouple is formed as a probe so that the thermocouple wire itself comes into contact with the surface to be measured. Even with such a probe construction, in the case that a work piece is integrally formed from an electrically conductive material, tips of both the thermocouples may be constructed by the probes, or one of tips is constructed by the probe, and the other tip is connected to a suitable portion of the work piece. In the case that a work piece is formed from a non-conductive material, tips of both the thermocouples are formed by the probes. In the case using at least one set of first and second thermocouples, moreover, it is possible to use a common thermocouple wire both as one of first and second thermocouple wires constituting the first measuring thermocouple and one of first and second thermocouple wires constituting the second measuring thermocouple. In general, moreover, in most cases a thermocouple is constructed by connecting tips of metal wires of different kinds to each other by spot welding or the like to form contacts having a volume although it is very small. In principle, the present invention can detect surface state of a surface to be measured using of a thermocouple having this configuration. However, as the thermoelectromotive force producing at the whole connected portions of metals of the two kinds constituting the thermocouples is used as an output, if the connected portion has a volume, the response and output characteristics may deteriorate. As described above, however, with the system bringing about the first and second thermocouple wires under the condition being spaced apart from each other into contact with the surface to be measured, the contact points between the surface to be measured and the probes of respective thermocouple wires, producing the thermoelectromotive force have no volume so that this system is advantageous for good response and output characteristics.

The method and device for detecting surface state according to the invention can detect surface states (surface roughness Ry and/or surface temperature variation ΔT) of all work pieces without any limitation, insofar as the work piece has been subjected to surface working (machining such as cutting, grinding or the like) or surface processing (physical or chemical treatment such as rolling, skin pass rolling, coating or the like) (the surfaces to be measured have been subjected to the surface working or surface processing). Particularly, the method and device according to the invention can more effectively detect surface state of an electrically conductive work piece, or at least having a conductive surface to be measured. It is preferable that the measurement of the thermoelectromotive force by the measuring thermocouple is carried out, and simultaneously therewith surface working or processing of the work piece is performed. In practice, it is preferable to arrange measuring means (measuring thermocouples) on the line of the surface working or processing. With the method and device according to the invention, the shapes of the surfaces to be measured are not limited for detecting the Ry and ΔT, while the conditions of the work piece being detected are not limited (in more detail, the detection can be effected regardless of the conditions of the work piece, such as moving, for example, rotating, or stationary). In other words, the Ry and ΔT can be detected by the method and device according to the invention as long as the detecting configuration is ensured to enable frictional heat to be generated by the contact between the measuring thermocouples and the surface to be measured (in the case using at least one set of first and second measuring thermocouples as measuring means, the detecting configuration enabling frictional heat to be generated by the contact between the surface to be measured and at least one of the first and second measuring thermocouples). Even with the case that the surface to be measured is two or three dimensional curved surface (surface of rotation such as spherical surface, circular cylindrical surface such as outer or inner surface of a cylindrical work piece, or concave surface, convex surface and the like) or flat surface, uneven surface or concave and convex surface, and the like, the method and device can properly detect the Ry and ΔT by arranging the measuring thermocouples in a manner that they are moved relatively to the surface to be measured under contact condition at a constant pressure. In case of a work piece rotating or linearly moving, the measuring thermocouples may be adapted to contact the surface to be measured at a constant pressure at a constant position on the moving path of the surface to be measured. In the case of a work piece in a stationary condition, moreover, the measuring thermocouples may be adapted to move on the surface to be measured under the contact condition therewith at a constant pressure. In the case that a work piece is eccentrically rotating, or a surface to be measured is uneven or a convex and concave surface, and further the contact points between the measuring thermocouples and the surface to be measured are being displaced in a direction crossing the direction of relative movement, the contact pressure between the measuring thermocouples and the surface to be measured can be maintained constant by enabling the measuring thermocouples to be reciprocally movable in the crossing direction.

Effect of the Invention

According to the method and device for detecting surface state of a work piece of the invention, the surface roughness and/or surface temperature variation of a surface to be measured can be detected from the thermoelectromotive force produced by bringing the measuring thermocouple into contact with the surface to be measured so that the surface state of the surface to be measured of the work piece being subjected to surface working or surface processing can be simply detected with high accuracy in an in-process or post-process manner without being affected by external disturbance such as temperature changes and the like in the detecting environment. Particularly, concerning a work piece of an electrically conductive material at least with its surface to be measured, the detection can be more effectively performed, and surface roughness and/or surface temperature variation of the surface to be measured can be detected more accurately in a real time manner. Even with the case that the surface roughness and/or surface temperatures of a surface to be measured are not distributed uniformly, by using a plurality of measuring thermocouples the distributing states can be accurately detected. In surface working (machining) such as grinding, the temperature of a work piece changes on proceeding of working so that the work piece gives rise to a deformation in micron or sub-micron range. Consequently, in order to give high dimensional accuracy and high accuracy of shape to a work piece, its thermal deformation must be accurately monitored. According to the invention, the state of the surface to be measured of a work piece can be detected on the working line or transfer line of the work piece so that such a monitoring can also be favorably and simply carried out. In the case that a surface to be measured is so narrow that a plurality of probes cannot be juxtaposed, insofar as a work piece is electrically conductive, the present invention can tolerate such a narrow object by connecting one of first and second thermocouple wires constituting the measuring thermocouple to part of the work piece other than the surface to be measured, and further by constituting both the thermocouples by three thermocouple wires by using one wire among three wires as a common wire both as one of the first measuring thermocouple wires and one of the second measuring thermocouple wires. Moreover, the present invention can preferably detect surface state of a surface of a work piece to be measured even if the work piece is in either of stationary and moving conditions or the work piece is in vibration condition. Further, when a work piece is a rolled steel and its surface roughness becomes greater on increasing its lot number due to impaired rolls, the increasing surface roughness can be accurately detected in a real time manner, thereby effectively preventing from producing a great amounts of defective products. Furthermore, the probes can be formed from a wear resistant material so that the durability of thermocouples can be improved, thereby enabling the favorable and high reliable detection of surface state for a long time.

DESCRIPTION OF THE REFERENCE NUMERALS

Figure 1:
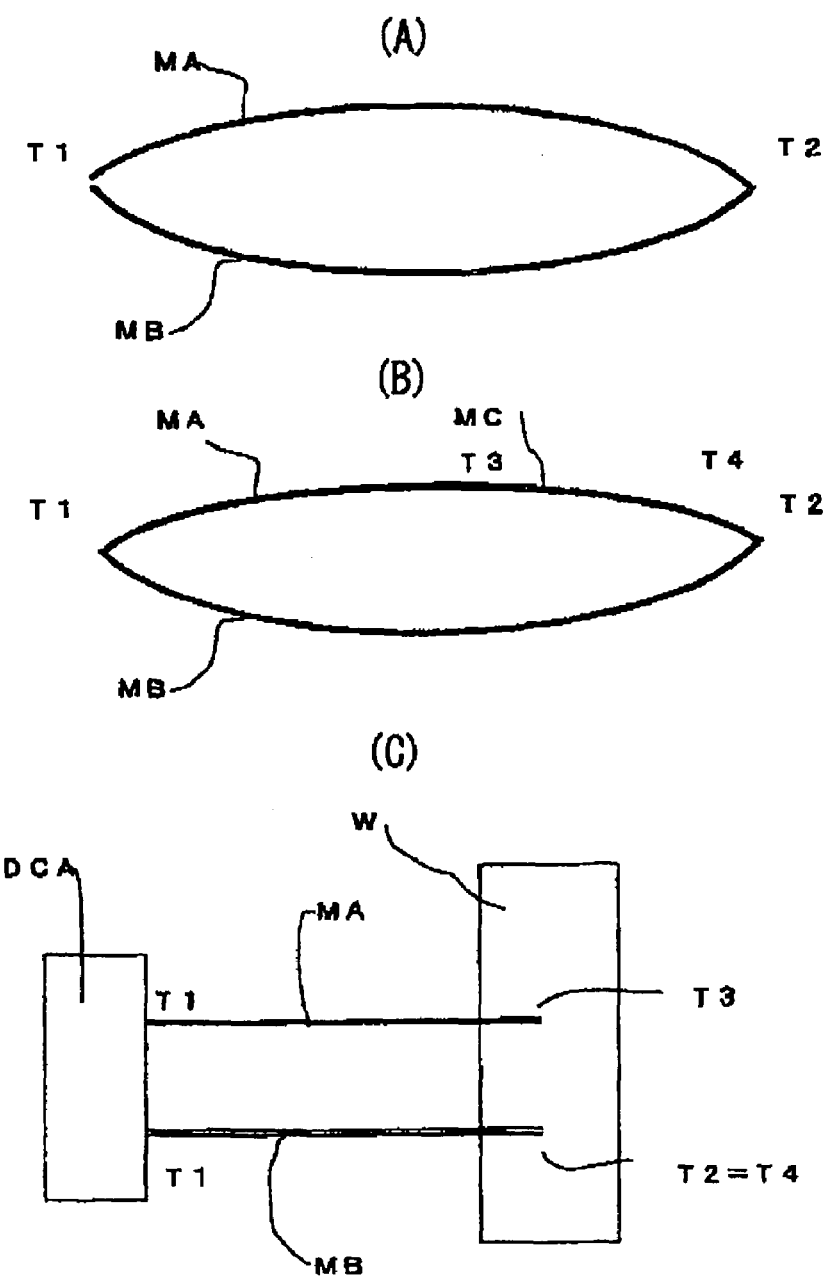
FIG. 1 is a view illustrating a model of a thermocouple for explaining the principle of measurement of a thermocouple thermometer.

1 Work piece
1a Surface to be measured
2 Measuring means
3 DC amplifier
4 Memory section
5 Arithmetic section
6 Information output section
7 First thermocouple
8 Second thermocouple

BEST MODE FOR CARRYING OUT THE INVENTION

Configuration of embodiments of method and device for detecting surface state of a work piece according to the invention will be explained in detail with reference to attached drawings hereinafter.

In the present invention, thermoelectromotive force caused by frictional heat on a work piece, mainly conductive body is measured by the use of thermocouples for detecting surface state of the work piece. First, therefore, the principle of temperature measurement using thermocouples will be simply explained. FIG. 1 illustrates a model of the thermometer of thermocouple type. As shown in FIG. 1(A), the temperature measurement is based on the Seebeck effect that with a closed circuit composed of two different kinds of metals MA and MB, if temperatures at two joined points of the two metals are T1 and T2 to produce a temperature difference (T1−T2), voltage correspondingly to the temperature difference (T1−T2) will occur between the metals to cause electric current flow. As shown in FIG. 1(B), even with the case that a metal MC of a different kind is inserted into the thermocouple, if temperatures T3 and T4 at the joined points are equal to each other (T3=T4), errors in measurement will not occur irrespective of components of the metal MC of the different kind without being affected by the insertion of the metal MC according to the law of intermediate metal. The temperature measurement in the present invention is carried out on the basis of such doctrines. Accordingly, for example, as shown in FIG. 1(C), when a CA wire thermocouple using an alumel wire (A wire) and a chromel wire (C wire) as different kinds of metals MA and MB is brought into contact with an electrically conductive work piece to be measured, one ends of the C wire and A wire are connected to a DC amplifier DCA, and temperatures at their joined points are T1. On the other hand, the work piece W can be thought of as the third different kind of metal MC inserted. The other ends of the C and A wires are at temperatures T2 and T3 which are the temperature T4 of the work piece (T2=T3=T4). In this way, the temperature measurement can be performed by the thermocouple contact system based upon the law of intermediate metal described above.

As described above, such a surface roughness measuring principle of the thermocouple contact system lies in the foundation of the present invention. The measuring principle will be explained in more detail prior to the explanation of the embodiment according to the invention.

Figure 2:
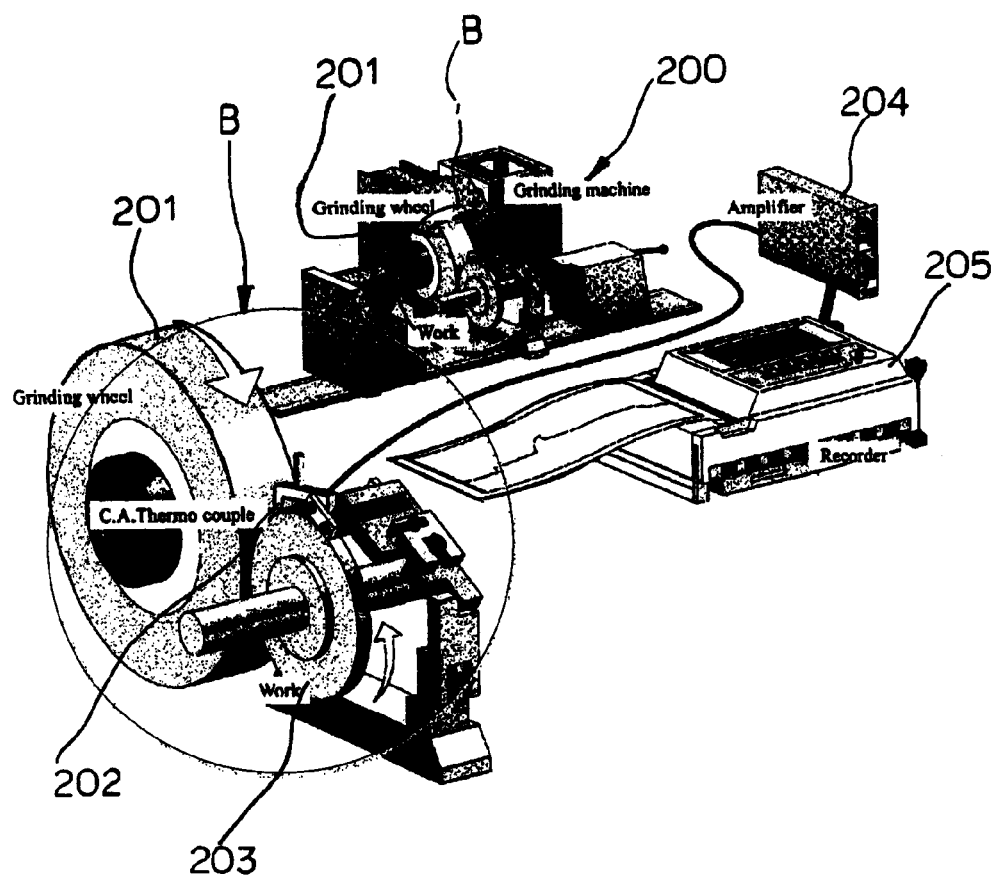
FIG. 2 is a perspective view illustrating a cylindrical grinding experimental device.

Confirmatory Experiments for the Surface Roughness Measuring Principle by Thermocouple Contact Type Thermometer FIG. 2 is a view illustrating outline of an experimental cylindrical grinding apparatus 200. In the experiment, the thermoelectromotive forces for different roughness of work pieces were measured by the use of the experimental cylindrical grinding apparatus 200 as shown in FIG. 2. Cylinder plunge grinding was performed using vitrified grinding wheels 201 in the experiment and the thermoelectromotive force producing principle of the thermocouple 202 was examined. As the thermocouple 202, only a thermocouple 202 made of C and A wires of a parallel wire contact type was arranged and connected through a DC amplifier 204 to a recorder 205 for the measurement. Moreover, a weight (not shown) was attached to probe head portion of the thermocouple 202 for stabilizing its contact state with a work piece 203.

Figure 3:
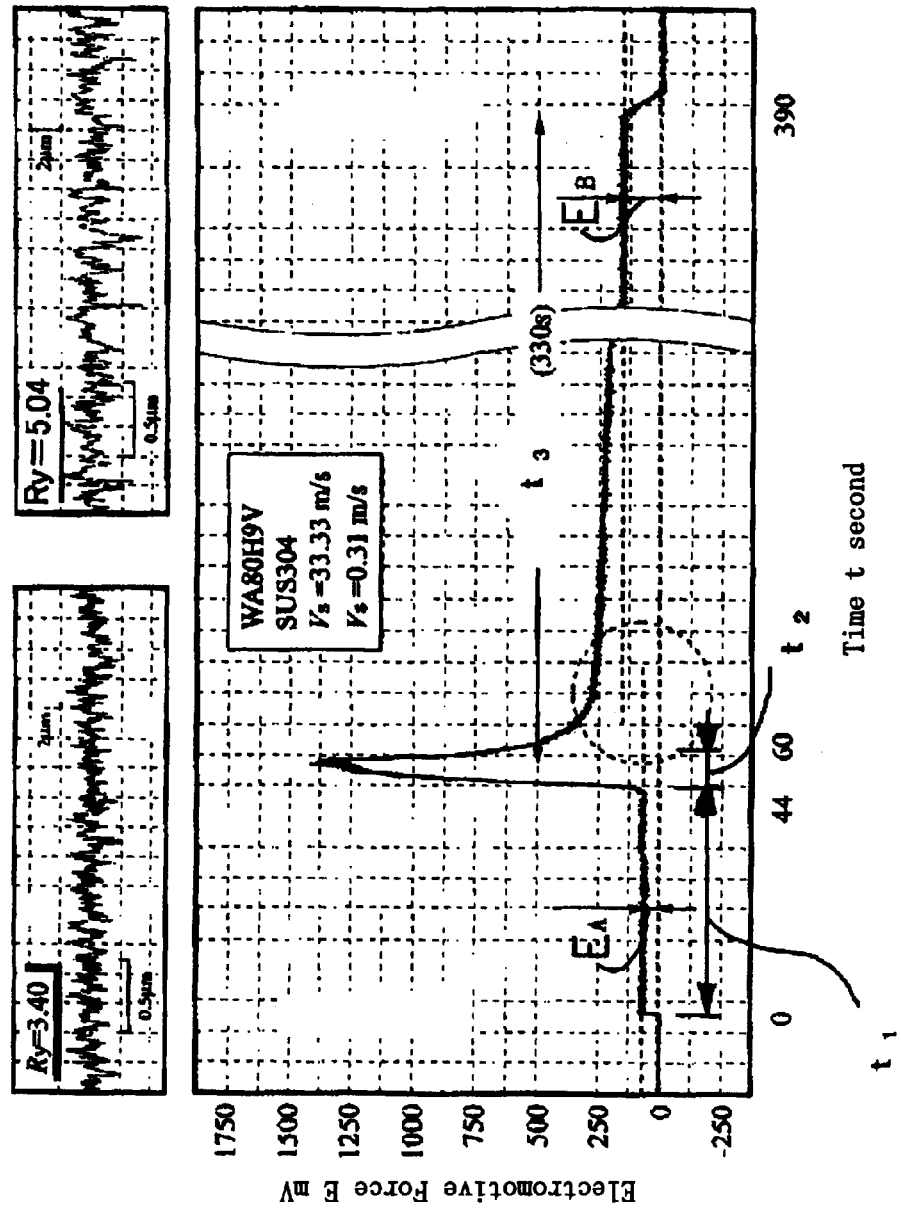
FIG. 3 is a graph illustrating changing process of thermoelectromotive force in the course of cylinder plunge grinding.

FIG. 3 illustrates changing process of the electromotive force in grinding process of cylinder plunge grinding by the experimental cylindrical grinding apparatus 200. Rotation starting region of the work piece 203 is denoted by $t_1$, and the grinding process of the work piece 203 is by $t_2$. As can be seen from this illustration, when the work piece 203 is started to be rotated, the thermoelectromotive force increases slightly and increases steeply in the cutting process zone from the thermoelectromotive force $E_A$ before cutting. Moreover, when the work piece 203 comes into a cooling period $t_3$ by rapidly retracting the wheel spindle stock, the thermoelectromotive force decreases rapidly and then decreases gradually, thereby finally being converged. Thereafter, when the rotation of the work piece 203 is stopped, the thermoelectromotive force becomes a value which is the same as that under the stopped condition of the work piece before grinding. Consequently, although the temperature of the work piece after approximately 330 seconds elapsed from the rapid retraction of the grinding wheel is the same as the temperature before grinding, the thermoelectromotive force $E_B$ is distinctly different from the thermoelectromotive force $E_A$. The surface roughness of the work piece after grinding is measured to find that the surface becomes rougher than that before being ground. It will be understood that the greater thermoelectromotive force is detected after grinding which corresponds to the fact that the surface roughness of the work piece becomes greater. Moreover, it is assumed that a zero point is the state that the rotation of the work piece 203 is stopped, and the difference between the thermoelectromotive force detected upon rotation of the work piece and the thermoelectromotive force at the zero point is determined as a thermoelectromotive force corresponding to the respective roughness.

It was envisioned that the surface roughness might affect the thermoelectromotive force in consideration of the experiment described above. Therefore, we examined in detail the relation between the surface roughness and the thermoelectromotive force.

Figure 4:
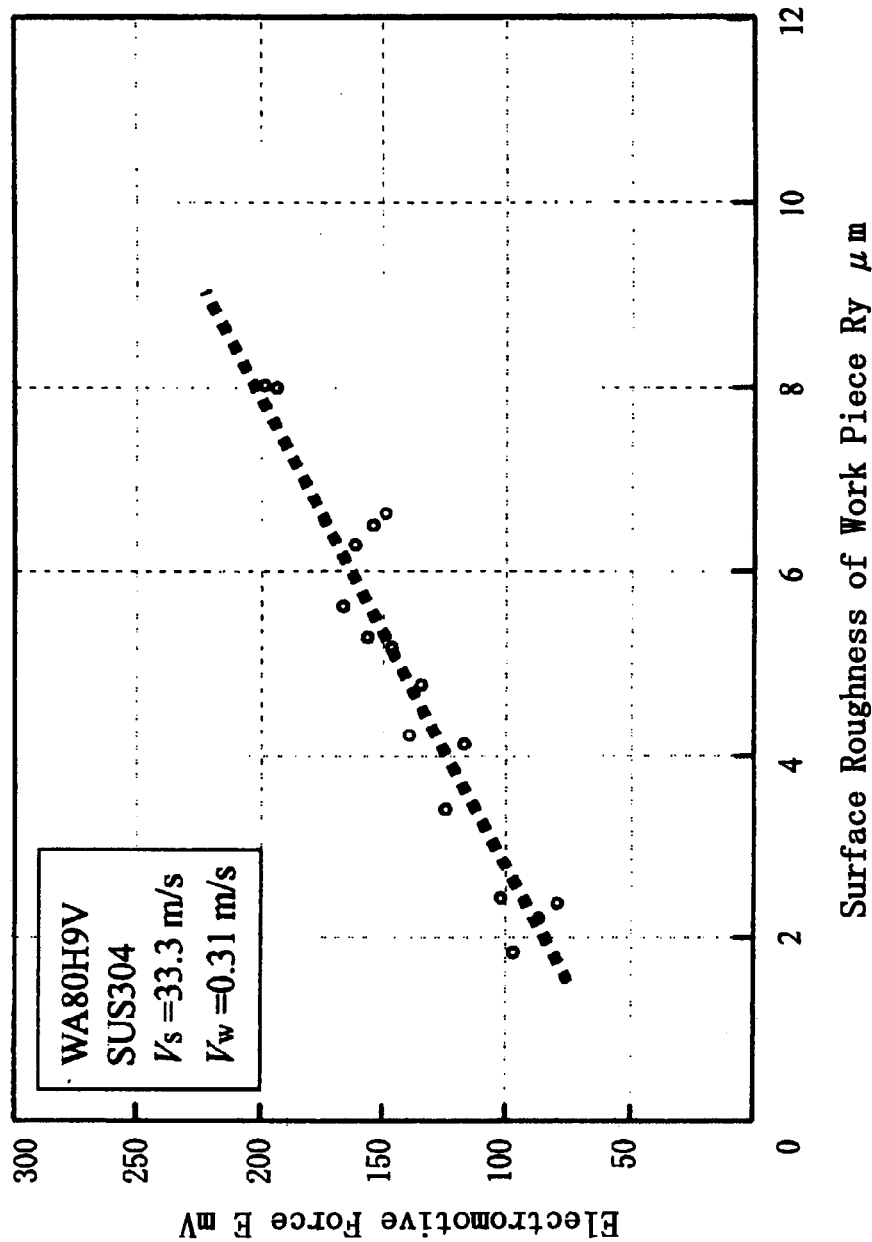
FIG. 4 is a graph illustrating variation in thermoelectromotive force with respect to respective surface roughness of various surfaces formed by cylindrical grinding.

Various surface roughness of work pieces were produced by the cylinder plunge grinding on the experimental cylindrical plunge grinding apparatus 200, and the thermoelectromotive forces at respective roughness were measured to study variations in thermoelectromotive force depending upon the surface roughness of the work pieces. FIG. 4 illustrates variations in electromotive force depending on various surface roughness of work pieces. As can be seen in FIG. 4, the greater the surface roughness of work piece, the greater becomes the thermoelectromotive force, and totally the thermoelectromotive force linearly increases. Accordingly, it becomes possible to measure the surface roughness of work pieces with higher accuracy from the thermoelectromotive force. This is the essential part for the method for measuring surface roughness with thermocouples contacting the work pieces according to the invention.

Figure 5:
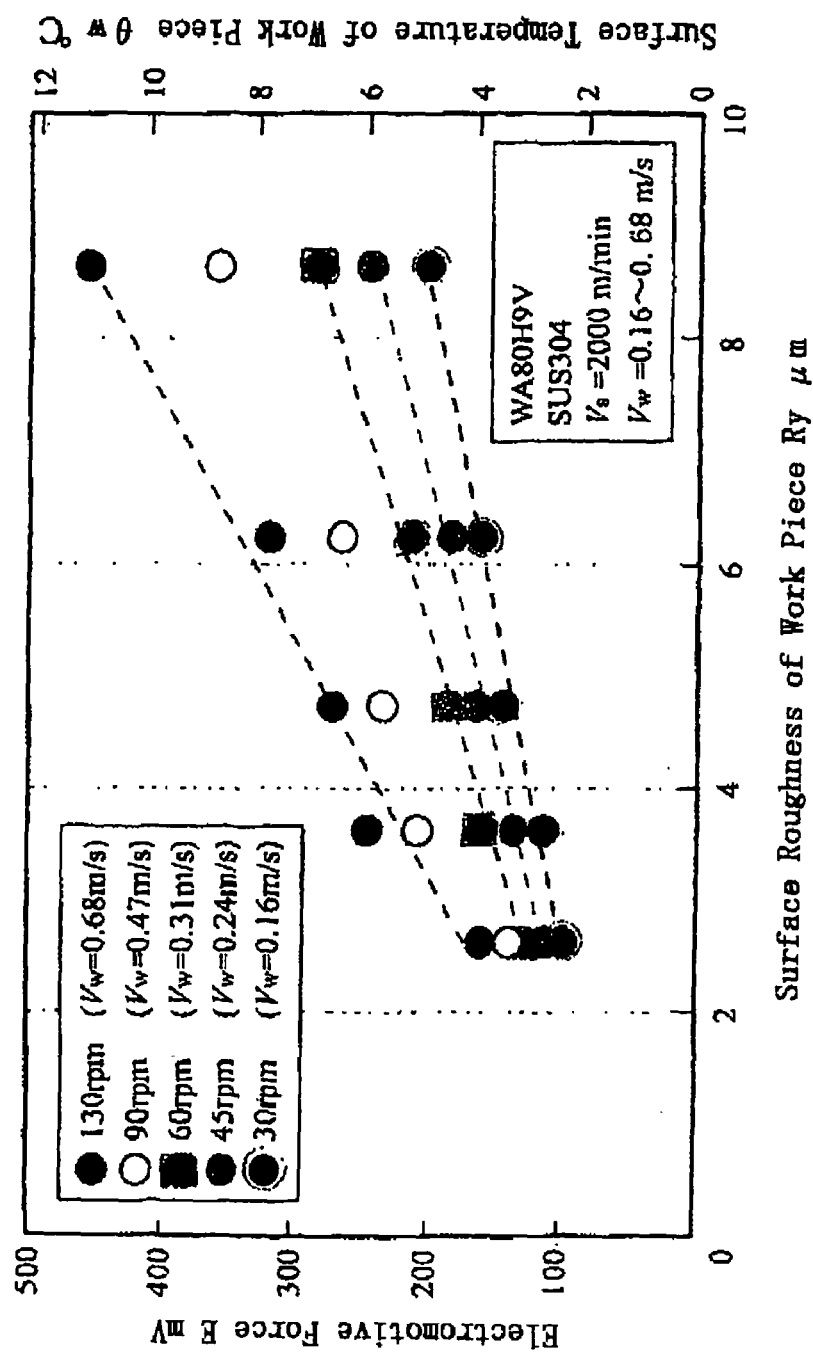
FIG. 5 is a graph illustrating variation in thermoelectromotive force produced by variation in work piece surface roughness and work circumferential speed.

Thereafter, variation in thermoelectromotive force was measured which was caused by variation in surface roughness and circumferential speed of work pieces. FIG. 5 is a graph illustrating the results of the measurements. As can be seen from FIG. 5, the surface roughness of work pieces and the thermoelectromotive forces are in a liner relationship and it will be understood that with respect to surface roughness, the greater the circumferential speeds of the work pieces, the greater become the detected thermoelectromotive forces. It can be thought that as the circumferential speed becomes greater, the amount of frictional heat becomes larger so that the detected thermoelectromotive force becomes greater. Moreover, as the circumferential speed becomes greater, the gradients of the linear relation become gradually steeper.

From the result of the confirmatory experiments described above, the measurement principle of surface roughness of the thermocouple contact type according to the invention has the following characteristics and application ranges.

1. The Range of Materials

The measurement of roughness is possible for all the electrically conductive materials. It is desirable that a specific electric resistance of the material of the surface to be measured is less than a few $\mu\Omega$cm.

2. The Range of Measuring Speed

The measuring method according to the invention can be effected within a range of 0.01 nm/sec. to 10 m/sec. of probe scrubbing speed, more preferably within a range of 0.1 m/sec. to 5 m/sec. in consideration of wear and the like, and even more preferably within a range of 0.15 m/sec. to 1 m/sec. in consideration of measuring output accuracy. In comparison with the prior art, measuring speed of the prior art stylus roughness meter is of the order of 3 mm/sec. even at the maximum, and the speed of non-contact roughness meter is of the order of 5 mm/sec. even at the maximum (sampling resolving power in the measuring direction being of the order of 47 $\mu$m), while measuring speed of typical commercially available non-contact roughness meters is substantially the same as the speed of the stylus roughness meter described above.

3. The Range of Temperature in Measurement

The measuring method according to the invention is capable of measuring in atmosphere at $-10°$ C. to $200°$ C. Particularly, within this temperature range, roughness measurement can be carried out even with the case that the temperature at the surface to be measured is rapidly changed during the measurement. Moreover, although the temperature changes at the surface to be measured are included in the output of the thermoelectromotive force in the roughness measurement according to the invention, temperature canceling becomes possible by using two or more kinds of thermocouples as later described so that the surface roughness can be output irrespective of temperature measurement.

In the stylus roughness meter and non-contact roughness meter of the prior art, on the other hand, these meters are generally used at a range of room temperature and in order to perform precise measurement, great care is required for restraining the temperature changes to about $\pm 1°$ C. using a constant temperature room for the purpose of avoiding extremely high or low temperatures and rapid temperature changes (a few degrees) during measurement.

4. Contact Condition between a Sensor and a Surface to be Measured (Treatment of the Surface to be Measured when Measuring)

In the case that the surface to be measured is under stable condition, the measuring method according to the invention is capable of performing measuring operation irrespective of dried condition and wet condition (by liquid such as water and oil or semiliquid material other than acid and alkali medicals).

Particularly, the wet condition is preferable, if such a condition can be obtained. On the other hand, the stylus roughness meter and non-contact roughness meter of the prior art are tedious and time-consuming to remove oil, clean, and dry for measurement of the surface.

5. Shape and Configuration of Roughness Sensor

It is preferable that the sensor (thermocouple material) has a configuration having the contact area with a surface to be measured, which is as large as possible in consideration of its output characteristics and having a comparatively smaller volume, and it is preferable to choose those fulfilling these conditions. If the contact area between the sensor and the surface to be measured becomes smaller, the amount of heating caused by the relative movement at the contact point between the sensor and the surface to be measured becomes smaller. If the volume of the sensor itself becomes larger, the heat transfer from the heat generating point at the contact point between the sensor and the surface to be measured is promoted to restrain the temperature rise at the heat generating point, resulting in lower output. As the sensor complying with the above requirements, generally thermocouple wires of a wire type are preferably used. In general, it is preferable to use thermocouple wires having a diameter of 0.1 mm to 1 mm, more preferably 0.3 mm to 0.7 mm, and even more preferable to use thermocouple wires having a square cross-section whose sides are 0.2 mm to 0.7 mm. Moreover, metal plates (lamellae) containing components of thermocouple materials and having a thickness of 0.1 mm to 1 mm may be used. Pins having a diameter of 0.1 mm to 1 mm may also be utilized (measurement being effected at the end face of the pin). Spherical or aggregated shape or the like may be used insofar as it fulfills the above conditions. Further, a thermocouple consisting of probes spaced from each other may be used irrespective of their shapes.

6. Materials of Thermocouple

Different metals of two kinds (one kind depending upon a system or method) can be used. Preferable are two sets of metals (chromel/alumel, chromel/constantan, and the like) which are combinations of metals of large thermoelectromotive force. As an alternative, a combination of a material to be measured and a metal of large thermoelectromotive force may be used. For example, in the case that the material to be measured is Fe, constantan wire is preferable.

7. Examples of Contact Configuration of the Probe with the Surface to be Measured (1) The thermocouple wires are subjected to a constant tensile force, and the thermocouple wires under such a condition are brought into contact with a surface to be measured at a constant pressure.

(2) The thermocouple wires are arranged along a guide (insulating material) having a predetermined shape, and the thermocouple wires under such a condition are brought into contact with a surface to be measured at a constant pressure.

(3) One side (edge) of a probe (thin plate, lamina) is brought into contact with a surface to be measured at a constant pressure.

(4) A thin plate (lamina) in the form of a circular disk is rotated at a predetermined speed or held under a freely rotatable, and its outer circumferential surface is brought into contact with a surface to be measured at a constant pressure.

(5) An end face of a probe pin is brought into contact with a surface to be measured at a constant pressure.

(6) Part of a probe of a shape other than those described above is brought into contact with a surface to be measured at a constant pressure.

Figure 6:
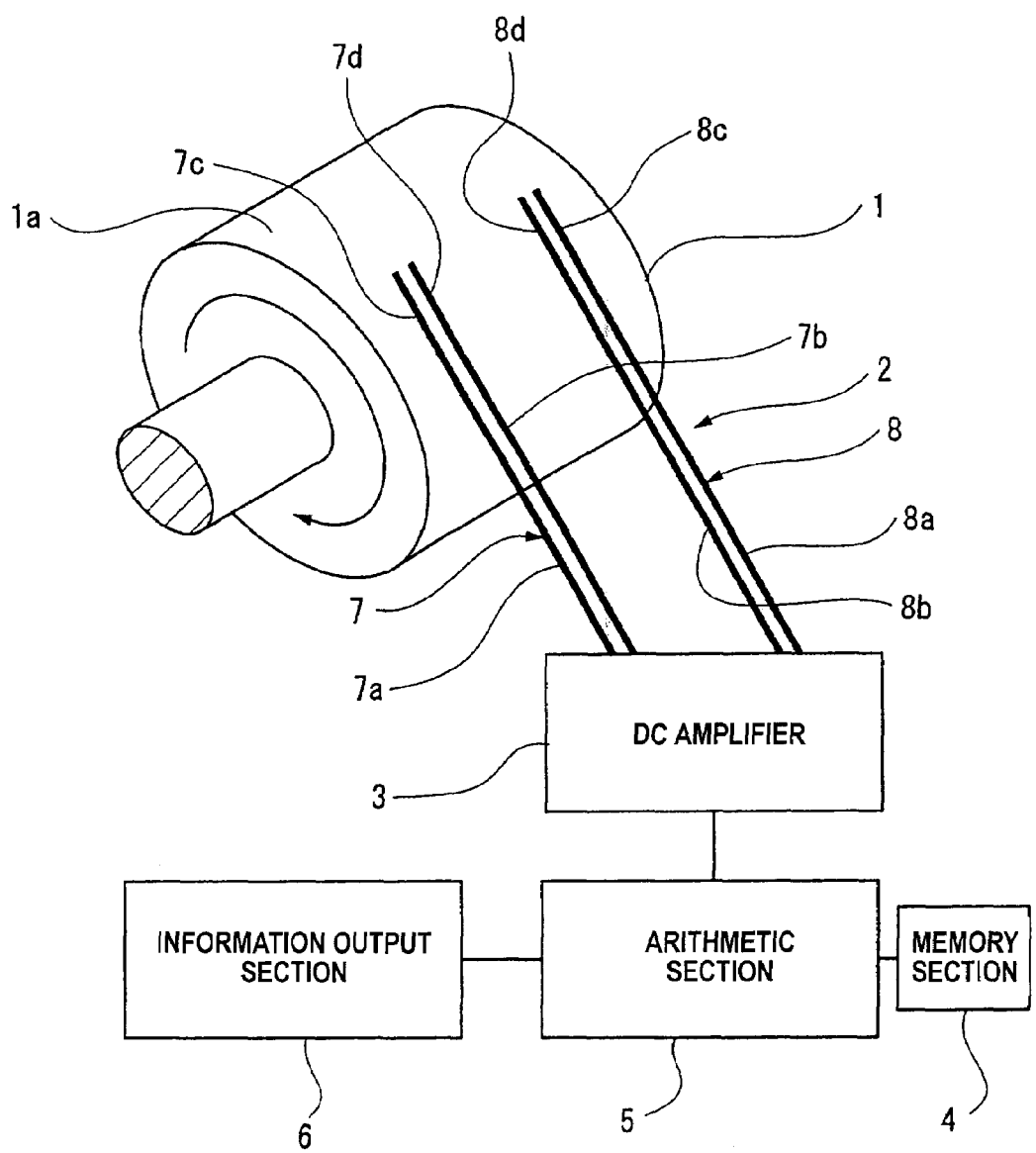
FIG. 6 is a perspective view illustrating one example of surface state detecting device according to the invention.

FIG. 6 illustrates one example of the device for detecting a surface state or condition of a work piece. This device (referred to hereafter as "first surface state detecting device") is used in the case that an outer circumferential surface of a work piece 1 is a surface 1a to be measured whose surface condition is detected. The first surface state detecting device comprises measuring means 2, a DC amplifier 3, and a controller including a memory section 4, an arithmetic section 5, an information output section 6. The work piece 1 is integrally formed from an electrically conductive material such as a metal or the like, whose outer circumferential surface as the surface 1a to be measured is subjected to machining such as grinding. The first surface state detecting device is attached to a working apparatus (referred to hereafter as "work piece working apparatus") such as a grinding machine so that the surface condition is detected, while the work piece 1 is being machined. As a control unit, for example, a personal computer, microcomputer or the like may be used. The DC amplifier 3 serves to amplify output signals (thermoelectromotive force) from the measuring means 2 to output the amplified signals to the computer. As the memory section 4, the memories of the computer are used, and as the arithmetic section 5 and the information output section 4, the arithmetic and output units including the central processing unit (CPU) of said computer are used. For example, the information output section 6 includes a display for displaying the information regarding results (surface roughness of measured surface 1a and/changes in surface temperature) effected in the arithmetic section 5, or output means for outputting data to a separate analyzer.

The measuring means 2 comprises a first measuring thermocouple 7 and a second measuring thermocouple 8 which are maintained in contact with the surface 1a to be measured at a constant pressure. The first measuring thermocouple 7 and the second measuring thermocouple 8 are different kinds of thermocouples from each other. For example, the first measuring thermocouple 7 consists of a first thermocouple wire 7a as chromel wire and a second thermocouple wire 7b as alumel wire, and probes 7c and 7d formed by the tips of both the thermocouple wires 7a and 7b are spaced in the width direction from each other and brought into contact with the surface 1a to be measured under the spaced condition. Moreover, the second measuring thermocouple 8 is constructed in the same manner as the first measuring thermocouple 7 with exception of the combination of component members as thermocouple wires 8a and 8b. The second measuring thermocouple 8 consists of the first thermocouple wire 8a as chromel wire and the second thermocouple wire 8b as constantan wire and probes 8c and 8d formed by the tips of both the thermocouple wires 8a and 8b are spaced in the width direction from each other and brought into contact with the surface 1a to be measured under the spaced condition. The first and second measuring thermocouples 7 and 8 are brought into contact with the surface 1a so as to be in parallel with each other side by side in the width direction of the surface 1a to be measured. The contact pressures of the respective measuring thermocouples 7 and 8 against the surface 1a to be measured are set to a constant pressure irrespective of the rotation of the work piece 1. The contact pressures of the first measuring thermocouple 7 and the second measuring thermocouple 8 are set to the same values.

The memory section 4 stores correlation data between the thermoelectromotive force and surface roughness and/or surface temperature variation previously obtained by the first and second data collecting thermocouples. The correlation data are collected by the use of the first surface state detecting device in the following manner. Namely, instead of the work piece 1, a standard work piece of the same shape and material as those of the work piece 1 is set on said work piece working apparatus and is rotated at a speed the same as that at which the work piece 1 is machined. With the standard work piece being rotated, the thermoelectromotive force is measured by the first measuring thermocouple 7 used as a first data collecting thermocouple and the second measuring thermocouple 8 used as a second data collecting thermocouple to obtain correlation data between the thermoelectromotive force, surface roughness of the standard surface as the outer circumferential surface of the standard work piece, and surface temperature variation and to cause the memory section 4 to memorize the obtained correlation data. The surface roughness of the standard surface is already known by measuring it by a common method. Moreover, the surface temperature variation is also known by the procedure in the same manner for collecting the correlation data, while adjusting the temperature of the standard work piece by a suitable temperature adjuster. By using the first surface state detecting device in this way, a first correlation data $\Delta E = \alpha 1 \cdot \Delta T + \beta 1 \cdot Ry$ and a second correlation data $\Delta E = \alpha 2 \cdot \Delta T + \beta 2 \cdot Ry$ can be obtained by causing relative movement of the first data collecting thermocouple the same as the first measuring thermocouple 7 and the second data collecting thermocouple the same as the second measuring thermocouple 8 with respect to the standard work piece under the condition of the first and second data collecting thermocouples in contact with the standard surface whose surface roughness and/or surface temperature are already known, on the same contact conditions (contact pressure and the like) and the same relative movement conditions (circumferential speed of the standard work piece) as those in the case of the first and second measuring thermocouples 7 and 8 and the surface 1a to be measured. In this case, $\alpha 1$ is the inherent temperature coefficient of the first data collecting thermocouple (first measuring thermocouple 7), while $\alpha 2$ is the inherent temperature coefficient of the second data collecting thermocouple (second measuring thermocouple 8). Further, $\beta 1$ is the roughness coefficient derived from the relation between the thermoelectromotive force and the surface roughness depending upon the contact condition and relative movement condition between the first data collecting thermocouple and the standard surface (the same as the contact condition and relative movement condition between the first measuring thermocouple 7 and the surface 1a to be measured). And, $\beta 2$ is the roughness coefficient derived from the relation between the thermoelectromotive force and the surface roughness depending upon the contact condition and relative movement condition between the second data collecting thermocouple and the standard surface (the same as the contact condition and relative movement condition between the second measuring thermocouple 8 and the surface 1a to be measured).

And after such correlation data have been collected and caused the memory section 4 to memorize the collected data, the work piece 1 is set on the work piece working apparatus to start the working of the work piece 1 for measuring the thermoelectromotive force by the measuring means 2. In this manner, from the thermoelectromotive force $\Delta E1$ measured by the first measuring thermocouple 7 and the thermoelectromotive force $\Delta E2$ measured by the second measuring thermocouple 8, the surface roughness Ry of the surface 1a to be measured and/or surface temperature variation $\Delta T$ is detected in a real time manner by the arithmetic section 5 on the basis of the correlation data. The detected surface roughness and temperature variation are displayed and output in the information output section 6. In the arithmetic section 5, the following calculation is carried out.

In the arithmetic section 5, namely, the surface roughness Ry is obtained as $Ry = (\alpha 2 \cdot \Delta E1 - \alpha 1 \cdot \Delta E2)/(\alpha 2 \cdot \beta 1 - \alpha 1 \cdot \beta 2)$ by eliminating $\Delta T$ from the correlation formula $\Delta E1 = \alpha 1 \cdot \Delta T + \beta 1 \cdot Ry$ of the thermoelectromotive force $\Delta E1$ obtained by the first correlation data and the correlation formula $\Delta E2 = \alpha 2 \cdot \Delta T + \beta 2 \cdot Ry$ of the thermoelectromotive force $\Delta E2$ obtained by the second correlation data. Moreover, the temperature variation $\Delta T$ is obtained as $\Delta T = (\beta 2 \cdot \Delta E1 - \beta 1 \cdot \Delta E2)/(\alpha 1 \cdot \beta 2 - \alpha 2 \cdot \beta 1)$ by eliminating Ry from both the correlations data.

Figure 7:
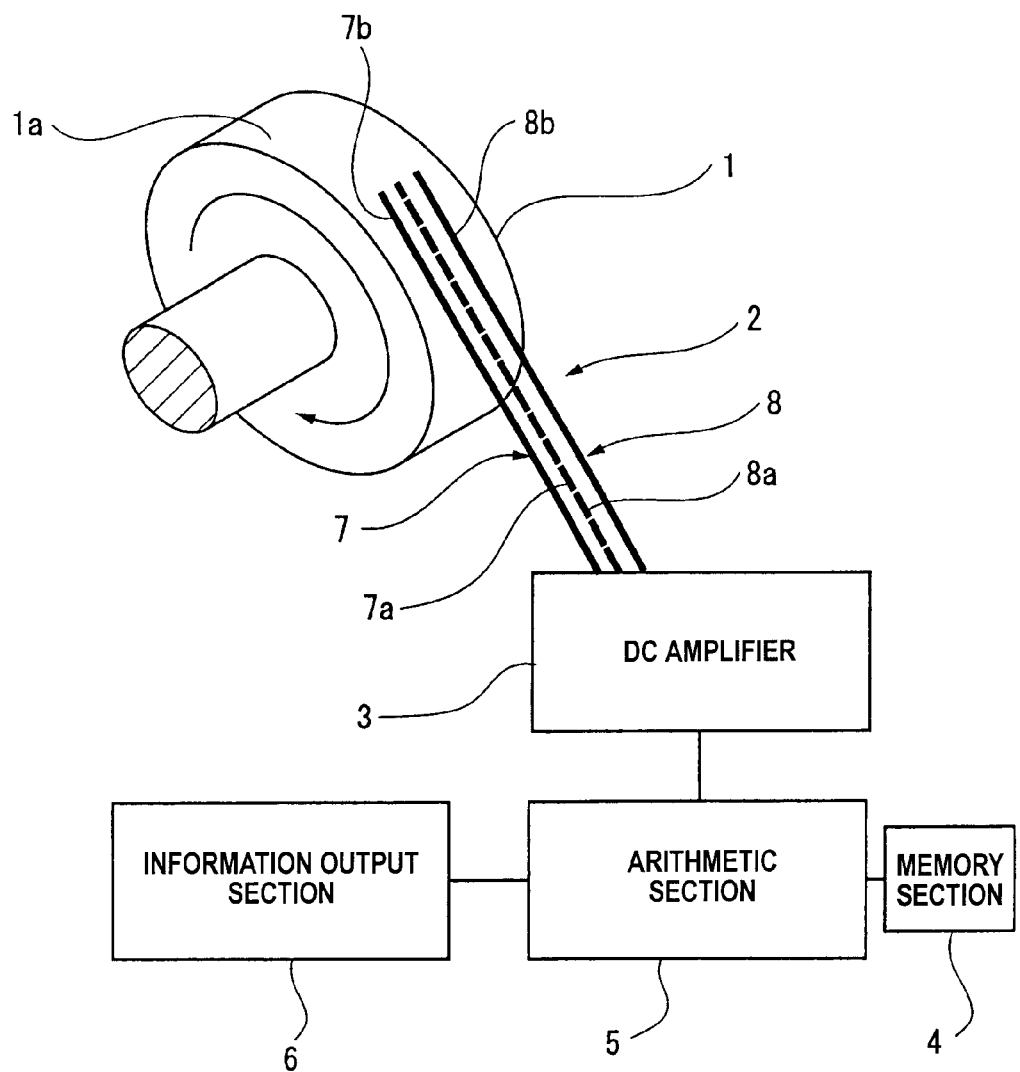
FIG. 7 is a perspective view illustrating a modification of the surface state detecting device.

With the first surface state detecting device, and now, in the case that a width of the surface 1a to be measured is not sufficient to arrange both the measuring thermocouples 7 and 8 in parallel with each other side by side, a common thermocouple wire is used both as one of the thermocouple wires 7a and 7b constituting the first measuring thermocouple 7 and one of the thermocouple wires 8a and 8b constituting the second measuring thermocouple 8 so that even if the surface 1a to be measured is narrow, the two thermocouples can be juxtaposed. In the case that, for example, the first measuring thermocouple 7 consists of the first thermocouple wire 7a of chromel wire and the second thermocouple wire 7b of alumel wire and the second measuring thermocouple 8 consists of the first thermocouple wire 8a of chromel wire and the second thermocouple wire 8b of constantan wire, the first thermocouple wires 7a and 8a are made of common thermocouple wire as shown in FIG. 7.

Figure 8:
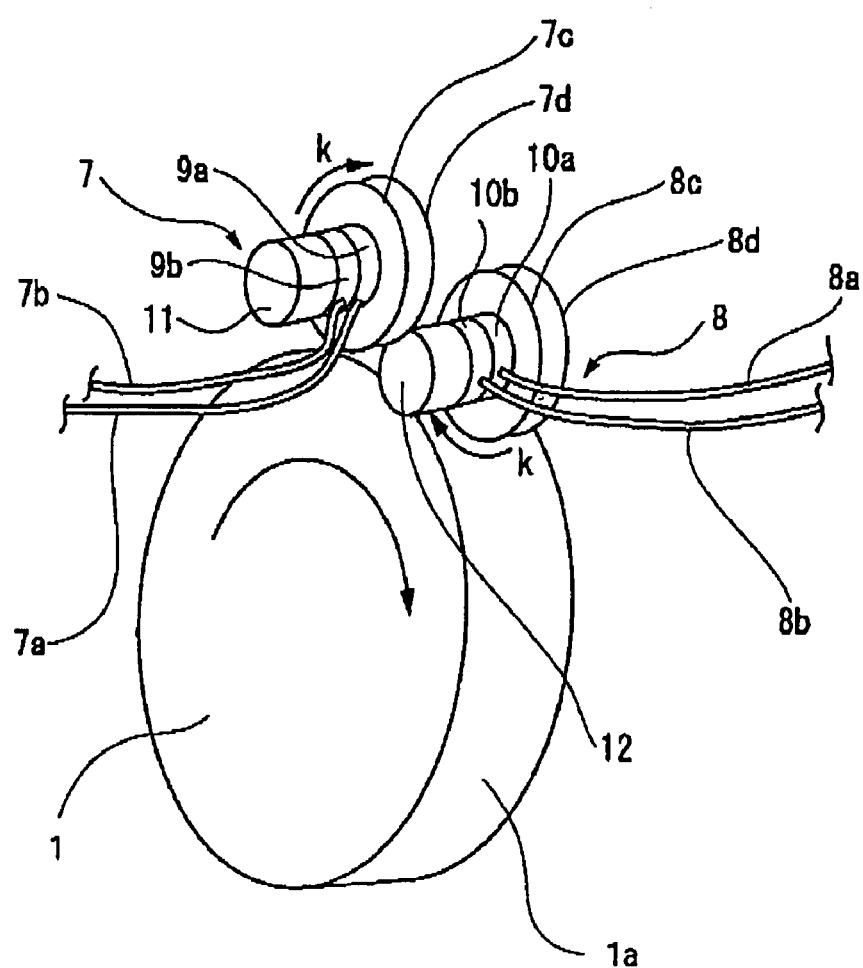
FIG. 8 is a perspective view illustrating another modification of the surface state detecting device.

FIG. 8 illustrates a modification of the device for detecting surface state of a work piece according to the invention. This device (referred to hereafter as "second surface state detecting device") has a substantially same construction as that of the first surface state detecting device except for probes 7c, 7d and 8c, 8d of first and second thermocouples 7 and 8, which are circular disk of a metal.

In other words, as shown in FIG. 8, the first measuring thermocouple 7 (or the second measuring thermocouple 8) comprises rotatable probes 7c and 7d (or probes 8c and 8d) in the form of a circular disk arranged on the same axis in parallel with and insulated from each other. On the rotating shaft of the probes 7c and 7d (or probes 8c and 8d) rotating rings 9a and 9b are relatively rotatably fitted and held and electrically connected to the probes 7c and 7d, respectively. The first thermocouple wire 7a (or first thermocouple wire 8a) is connected to one rotating ring 9a (or rotating ring 10a), while the second thermocouple wire 7a (or second thermocouple wire 8b) is connected to the other rotating ring 9b (or rotating ring 10b). Both the probes 7c and 7d (or probes 8c and 8d) are rotationally driven by a suitable drive motor 11 (or drive motor 12) such as a stepping motor so as to generate relative speed at contact points between the surface 1a to be measured and the probes. In other words, the probes 7c and 7d (or the probes 8c and 8d) are rotated by means of the motor 11 (or motor 12) in a direction reverse (direction k in FIG. 8) to the rotating direction of the surface 1a to be measured. In the case that the probes 7c and 7d (or the probes 8c and 8d) are rotated in the same direction (reverse to the direction k in FIG. 8) as the rotating direction of the surface 1a to be measured, the probes 7c and 7d (or the probes 8c and 8d) are rotated so that the circumferential speeds of the probes 7c and 7d (or the probes 8c and 8d) are different from that of the work piece 1.

With the second surface state detecting device of such a construction, the thermoelectromotive forces $\Delta E1$ and $\Delta E2$ can be measured by means of the first and second measuring thermocouples 7 and 8 so as to obtain said correlation data to acquire the surface roughness Ry $(=(\alpha 2 \cdot \Delta E1 - \alpha 1 \cdot \Delta E2)/(\alpha 2 \cdot \beta 1 - \alpha 1 \cdot \beta 2))$ of the surface $1a$ to be measured and/or surface temperature variation $\Delta T$ $(=(\beta 2 \cdot \Delta E1 - \beta 1 \cdot \Delta E2)/(\alpha 1 \cdot \beta 2 - \alpha 2 \cdot \beta 1))$ from the thermoelectromotive forces $\Delta E1$ and $\Delta E2$ in the arithmetic section 5 in the same manner as the first surface state detecting device.

In the second surface state detecting device, the first and second measuring thermocouples 7 and 8 can be the same kind of thermocouples (materials and constructions of the thermocouple wires and probes can be the same). Namely, the correlation data are obtained and the thermoelectromotive forces are measured by the use of different contact conditions and/or different relative movement conditions of the first and second measuring thermocouple 7 and 8 to the surface $1a$ to be measured (or the standard surface).

First, for example, the probes $7c$, $7d$ and $8c$, $8d$ are rotationally driven by motors 11 and 12 such that their circumferential speeds or the rotating directions are different from each other, thereby obtaining correlation data. Since the first and second measuring thermocouples 7 and 8 are of the same kind, and temperature coefficients are the same value $\alpha 1$, the first correlation datum is $\Delta E = \alpha 1 \cdot \Delta T + \beta 1 \cdot Ry$ and the second correlation datum is $\Delta E = \alpha 1 \cdot \Delta T + \beta 2 \cdot Ry$. Subsequently, by measuring the thermoelectromotive forces $\Delta E1$ and $\Delta E2$ by the use of the first and second measuring thermocouples 7 and 8, the surface roughness of the surface $1a$ to be measured $Ry = (\alpha 1 \cdot \Delta E1 - \alpha 1 \cdot \Delta E2)/(\alpha 1 \cdot \beta 1 - \alpha 1 \cdot \beta 2) = (\Delta E1 - \Delta E2)/(\beta 1 - \beta 2)$ can be calculated and surface temperature variation $\Delta T = (\beta 2 \cdot \Delta E1 - \beta 1 \cdot \Delta E2)/(\alpha 1 \cdot \beta 2 - \alpha 1 \cdot \beta 1)$ can be calculated in the arithmetic section.

With the second surface state detecting device, moreover, the surface state of the surface $1a$ to be measured can also be detected by rotationally driving the probes $8c$ and $8d$ of one measuring thermocouple (for example, the second measuring thermocouple 8) by the motor 10 under the condition that the rotating directions of the probes $8c$ and $8d$ are the same as that of the work piece 1 (or the standard work piece) and their circumferential speeds are the same as that of the work piece 1 (or the standard work piece 1).

Namely, when the probes $8c$ and $8d$ of the second measuring thermocouple 8 are rotationally driven under the condition described above, the relative speed at the contact point of the second measuring thermocouple 8 with the surface $1a$ to be measured becomes zero so that no frictional heat occurs. Accordingly, the first correlation datum becomes $\Delta E = \alpha 1 \cdot \Delta T + \beta 1 \cdot Ry$ and the second correlation datum becomes $\Delta E = 2\alpha \cdot \Delta T$. As a result, the surface roughness of the surface $1a$ to be measured $Ry = (\alpha 2 \cdot \Delta E1 - \alpha 1 \cdot \Delta E2)/(\alpha 2 \cdot \beta 1)$ and/or the surface temperature variation $\Delta T = \Delta E2/\alpha 2$ will be calculated from $\Delta E = \alpha 1 \cdot \Delta T + \beta 1 \cdot Ry$ and $\Delta E = 2\alpha \cdot \Delta T$ in the arithmetic section 5. On this occasion, if the first and second measuring thermocouples 7 and 8 are of the same kind, $\alpha 1$ is equal to $\alpha 2$ ($\alpha 1 = \alpha 2$), and the surface roughness Ry of the surface $1a$ to be measured is obtained as $Ry = (\Delta E1 - \Delta E2)/\beta 1$.

In the above case, moreover, in order that the relative speed at the contact point of the second measuring thermocouple 8 with the surface to be measured $1a$ becomes zero, the probes $8c$ and $8d$ of the second measuring thermocouple 8 may be rotationally driven under the condition described above, or the probes $8c$ and $8d$ may be rotatably supported without using the motor 11 so that the probes $8c$ and $8d$ are relatively rolled on the surface $1a$ to be measured (the standard surface).

Figure 9:
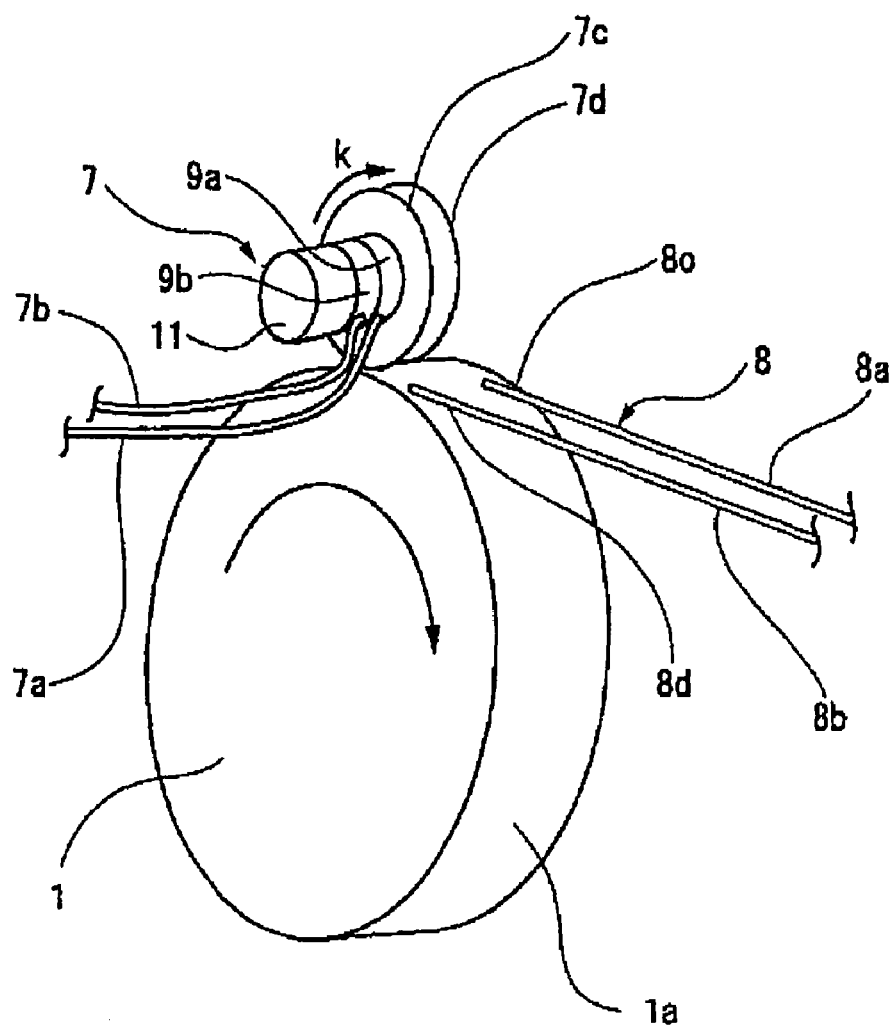
FIG. 9 is a perspective view illustrating a further modification of the surface state detecting device.

In the first or second surface state detecting device, as shown in FIG. 9 it may be possible that the probes $7c$ and $7d$ of one measuring thermocouple 7 are formed by circular metal disks connected to tips of the thermocouple wires, and the probes $8c$ and $8d$ of the other thermocouple 8 are formed by the tips themselves of the thermocouple wires. In this case, the circular disk probes $7c$ and $7d$ may be rotationally driven (or forced to rotate) by the motor 11 as shown in FIG. 9, or the probes $7c$ and $7d$ may be rotatably held as described above without providing the motor 11.

In the first and second surface state detecting devices, if the surface roughness of the surface to be measured $1a$ and/or surface temperature may vary widely and there is a need to detect their distributions, surface roughness and/or surface temperature variations at a plurality of locations on the surface $1a$ to be measured can be obtained at a time by bringing a plurality of sets of measuring thermocouples 7 and 8, one set being thermocouples 7 and 8, into contact with the surface to be measured $1a$ at it's a plurality of locations. Even with this case, the surface roughness Ry and/or the surface temperature variations $\Delta T$ can be detected using the respective sets of measuring thermocouples 7 and 8 in the same manner as described above.

In the first and second surface state detecting devices, furthermore, in the case that the surface temperature of the surface $1a$ to be measured is constant and its temperature variation $\Delta T$ is zero or known, the plurality of measuring thermocouples as described above need not be used, and the surface roughness of the surface $1a$ to be measured can be detected using one measuring thermocouple 7. In this case, the $Ry = \Delta E1/\beta 1$ is obtained in the arithmetic section 5 from the thermoelectromotive force $\Delta E1$ measured by the measuring thermocouple 7 on the basis of correlation data $\Delta E = \beta 1 \cdot Ry$ not having an item concerning the surface temperature.

Figure 10:
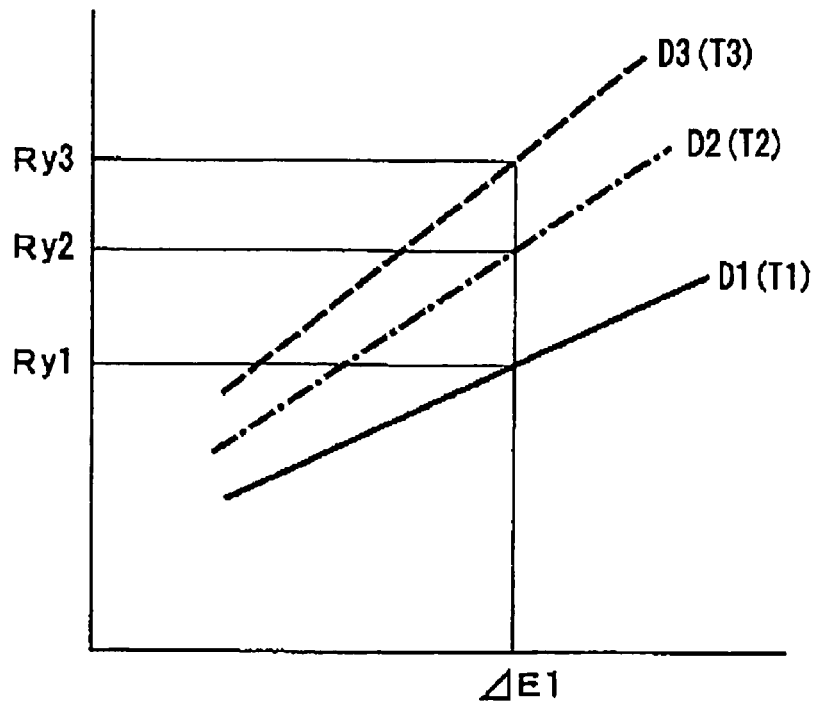
FIG. 10 is a graph illustrating correlation data between the thermoelectromotive force and surface roughness with surface temperature as a parameter.

In the case that only the surface roughness of the surface $1a$ to be measured is detected, moreover, the following method can be employed when the surface temperature of the surface to be measured is not known. Namely, first, by the use of the first or second state detecting device the thermoelectromotive force is measured by one thermocouple 7, while varying the temperature of the standard surface so that a plurality of data with surface temperature as a parameter are previously obtained as correlation data between the thermoelectromotive forces and the surface roughness. As shown in FIG. 10, for example, when the surface temperature is T1, T2 and T3, the respective correlation data D1, D2 and D3 are acquired and these data D1, D2 and D3 are memorized in the memory section 4. Then, the thermoelectromotive force $\Delta E1$ generated by the contact between the measuring thermocouple 7 and the surface $1a$ to be measured is measured by the measuring thermocouple 7, while the temperature of the surface $1a$ to be measured is measured by a suitable thermometer so that the surface roughness of the surface $1a$ to be measured is obtained in the arithmetic section 5 from the measured thermoelectromotive force $\Delta E1$ on the basis of the correlation data corresponding to the measured surface temperature T. As shown in FIG. 10, for example, when T is equal to T1 (T=T1), datum D1 is selected, on the basis of which the surface roughness Ry1 of the surface $1a$ to be measured is acquired. When T is equal to T2 (T=T2), datum D2 is selected, on the basis of which the surface roughness Ry2 of the surface $1a$ to be measured is acquired. When T is equal T3 (T=T3), datum D3 is selected, on the basis of which the surface roughness Ry3 of the surface $1a$ to be measured is acquired.

While the invention is not to be limited to the configurations of the respective embodiments described above, it will be understood by those skilled in the art that suitable modifications and improvements can be made therein without departing from the scope of the basic principle of the invention.

Figure 11:
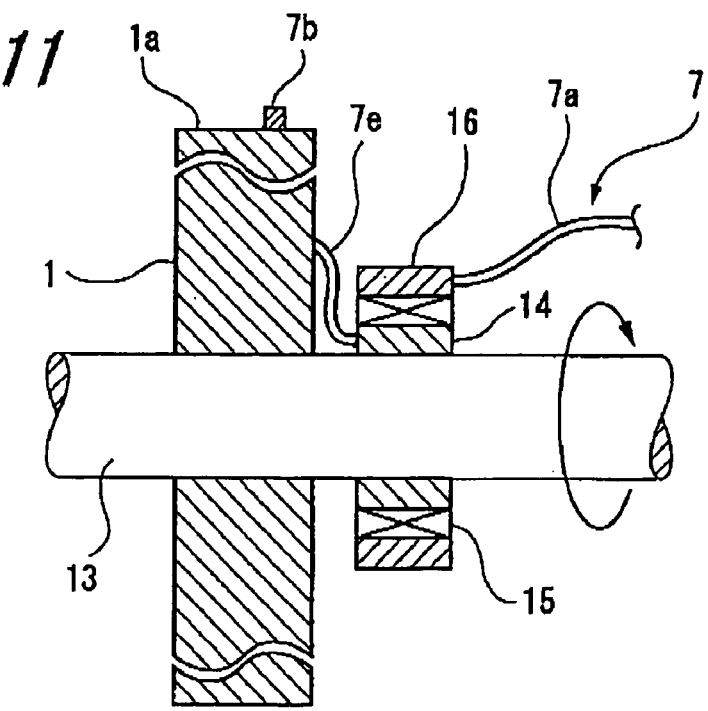
FIG. 11 is a longitudinal sectional view illustrating a modification of thermocouple.
Figure 12:
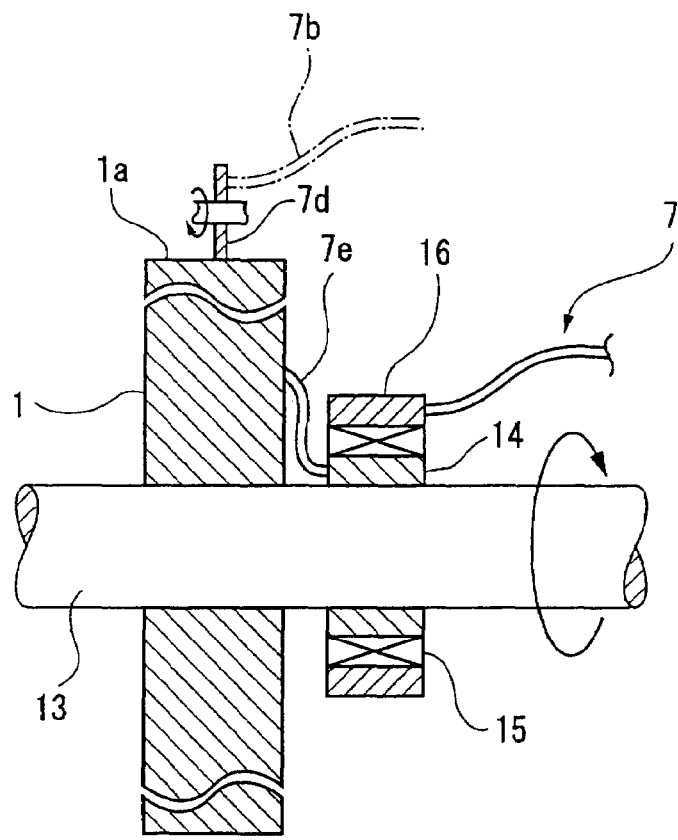
FIG. 12 is a longitudinal sectional view illustrating another modification of thermocouple.

For example, when the work piece 1 (and the standard work piece) is formed from an electrically conductive material, one thermocouple wire of the measuring and data collecting thermocouples may be connected to part of the work piece other than the surface 1a to be measured of the work piece. For example, the measuring thermocouple 7 of the type (tips themselves of the thermocouple wires being probes) used in the first surface state detecting device may be constructed as shown in FIG. 11. In other words, fitted on the rotating shaft 13 of the work piece 1 (or standard work piece) is a connecting ring 14 which is electrically connected through a connecting wire 7e to a side face of the work piece 1. Moreover, a rotating ring (slip ring) 16 is fitted outside the connecting ring 14 through a bearing 15 so as to be electrically connected to and rotatable relative to the connecting ring 14. Further, one thermocouple wire 7a constituting the measuring thermocouple 7 is connected to the rotating ring 16, while the tip end (probe) 7d of the other thermocouple wire 7b is brought into contact with the surface 1a to be measured. With the measuring thermocouple 7 of the type (using circular disc shaped probes) used in the second surface state detecting device, as shown in FIG. 12 one thermocouple wire 7a constituting the measuring thermocouple 7 is connected to the rotating ring 16, while the probe 7d of the other thermocouple wire 7b is constructed by a circular metal disk which is in contact with and rolling on the surface 1a to be measured. With the measuring thermocouple 7 thus constructed, the thermoelectromotive force can be measured in the same manner as with the thermocouple as described above.

Moreover, the detection of surface roughness and/or surface temperature variation according to the surface state detecting method and the surface state detecting device of the invention can also be preferably carried out on work pieces 1 having various shapes and performing various movements in the similar manner to those on the work piece 1 having a surface 1a to be measured of circular cylindrical surface and rotationally driven.

Figure 13:
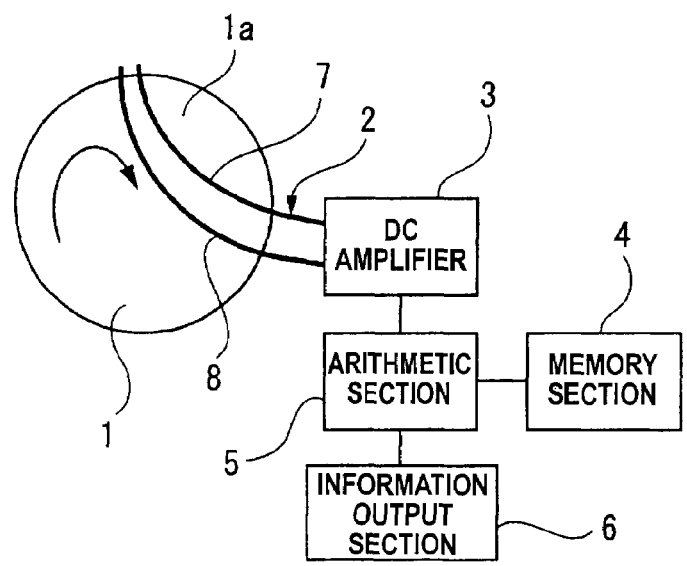
FIG. 13 is a schematic view illustrating the method for measuring surface state of a spherical work piece.

In other words, the work piece 1 or surface 1a to be measured are not to be limited by the work piece having the shape described above. The invention can detect surface state of work pieces having various three-dimensional shapes such as a surface 1a to be measured being spherical as shown in FIG. 13. When the output from the DC amplifier 3 connected to the thermocouples 7 and 8 is arithmetically processed in the arithmetic section 5 as described above, the correlation data can be corrected or amended depending upon shapes, contacting positions, rotating axis, rotating speeds, and the like, by previously inputting information regarding the shapes and the like of the surface to be measured and work piece 1.

Figure 14:
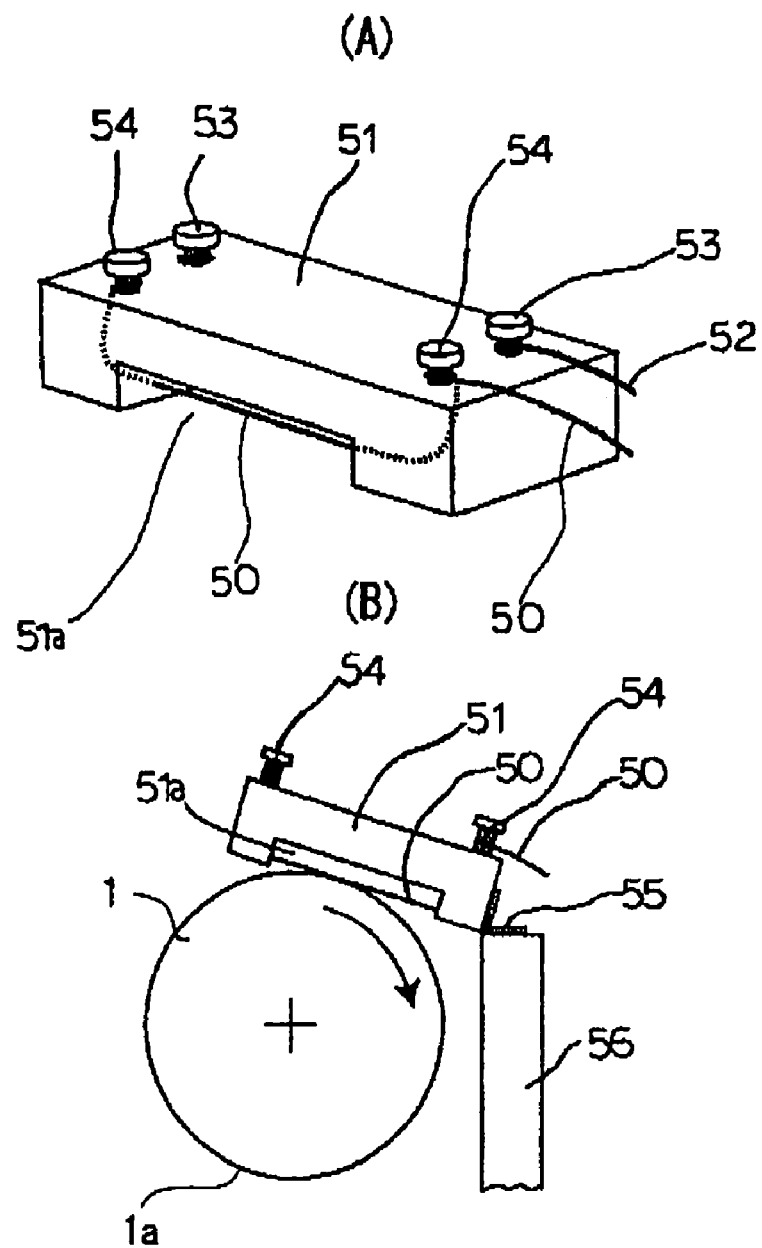
FIG. 14 are a perspective view (A) and a side view (B) illustrating a thermocouple including a tension applying member for applying a constant tension to the thermocouple.

As regarding the contact between the thermocouples and the work piece, if there are loosening and deformation of wires forming the probes, the contact condition becomes unstable to adversely affect the measuring accuracy. In order to preclude such an adverse affection, it is preferable to bring the thermocouple wires into contact with a work piece while applying a constant tensile force to the thermocouple wires as shown in FIG. 14(A). A tension applying member 51 is made from an insulating block body and has a recess 51a for holding thermocouple wires 50 and 52 subjected to tensile forces. The thermocouple wires 50 and 52 extend through the tension applying member 51 across the recess 51a and wound about a pair of reel screws 53 and 54. By tightening the reel screws 53 and 54, the CA wires can be linearly extended under a tension between the reel screws.

The tension applying member 51 is attached to a support member 56 located opposite to the work piece 1 by means of hinges 55 in a manner to be movable between a forward tilting position and an upright position relative to the work piece 1 as shown in FIG. 14(B). When the surface roughness is measured, the tension applying member 51 is pivoted from its upright position to the forward tilting position so as to abut against the rotating surface of the work piece 1 with the recess 51a facing downwardly and with the thermocouple wires under the tensile force. Therefore, as the weight of the tension applying member 51 acts on the wires, the thermocouple wires can be brought into contact with the work piece 1 on a constant load without loosening of the thermocouple wires so that stable in-process surface roughness measurement can be carried out.

Figure 15:
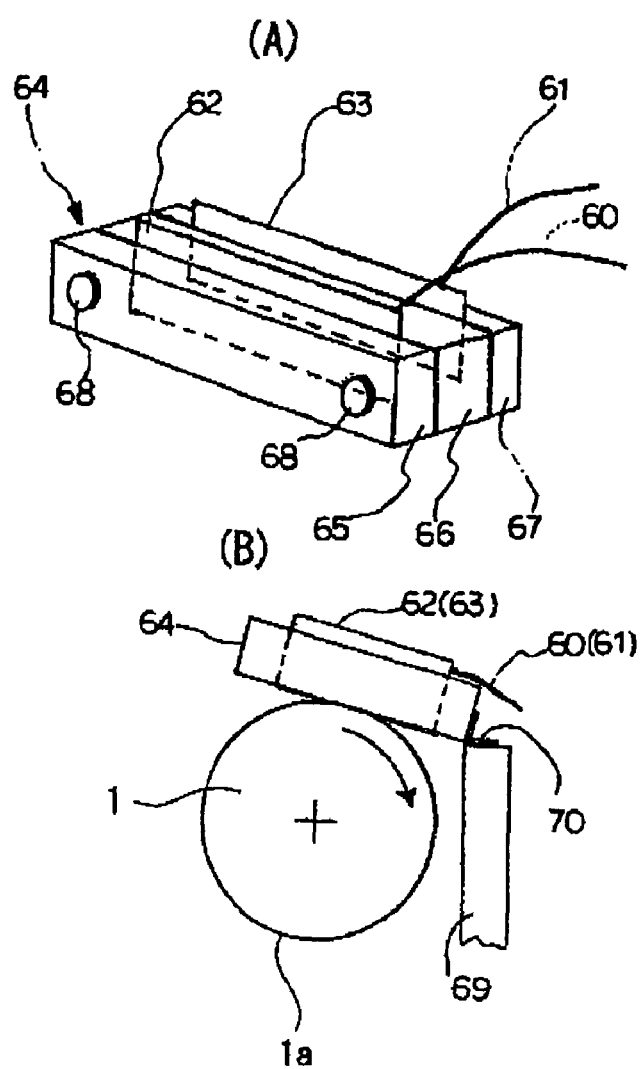
FIG. 15 are a perspective view (A) and a side view (B) illustrating a thermocouple comprising plate-shaped probes.

When thermocouple wires are directly used onto a work piece, loosening and deformation of wires may occur as described above. However, by holding the thermocouple materials of thin plates (lamellae) by a plate-shaped piece of high rigidity as shown in FIG. 15, there is no risk of the loosening and deformation. As shown in FIG. 15(A), to the tips of the thermocouple wires 60 and 61 plate-shaped conductive probes 62 and 63 are connected in an electrical continuity state. The respective plate-shaped probes 62 and 63 are embraced by insulating block pieces 65 to 67 and spaced apart from one another with predetermined distances. The plate-shaped probes 62 and 63 are fixed and held to the block pieces by means of set screws 68 such that their lower edges slightly extend from the insulating block pieces. An abutting block 64 having the insulating block pieces 65 to 67 embracing the plate-shaped probes 62 and 63 is attached to a support member 69 by means of hinges 70 so as to be movable between a forward tilting position and an upright position relative to the work piece 1 similarly to the configuration shown in FIG. 14. When the surface roughness is measured, the abutting block 64 including the respective plate-shaped probes 62 and 63 whose one edges slightly extend therefrom is pivoted into its forward tilting position so that the extending edges of the plate-shaped probes 62 and 63 are brought into abutment against the rotating surface 1a of the work piece 1. Therefore, the weights of the insulating block pieces and the plate-shaped probes act upon the work piece so that the respective plate-shaped probes can be brought into contact with the work piece on a constant load so that stable in-process surface roughness measurement can be carried out. In comparison with the thermocouples of wires, the holding plate-shaped probes 62 and 63 have a rigidity enabling the contact condition with the rotating object to be stably maintained.

Figure 16:
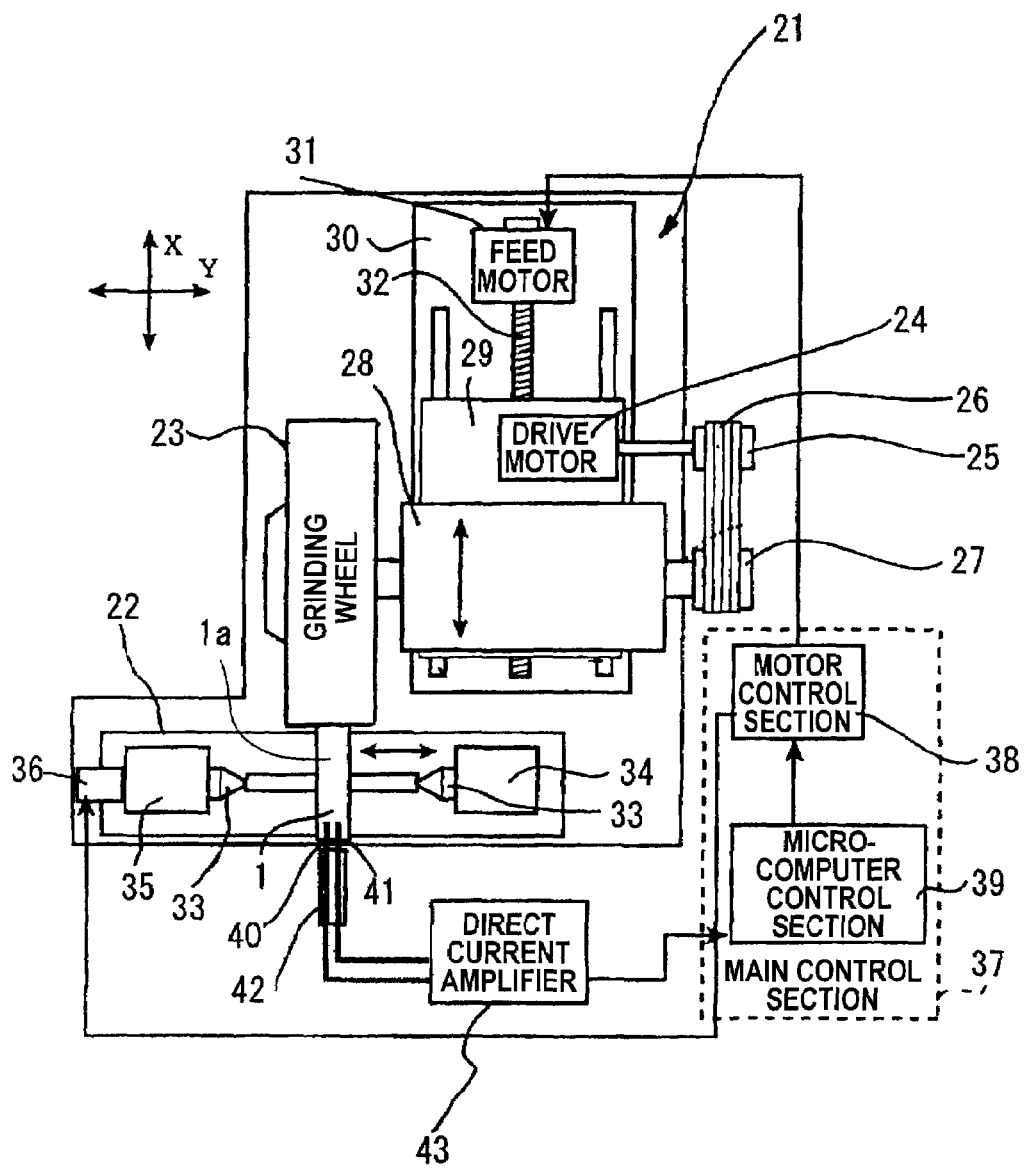
FIG. 16 is a plan view illustrating a practical example of surface state detection (in-process surface roughness measuring device for cylindrical grinding) according to the invention.

FIG. 16 illustrates a cylindrical grinding in-process surface roughness detecting device which is a practical example of the surface state detecting device according to the invention. This in-process surface roughness detecting device comprises a cylindrical grinding device 21 performing cylindrical grinding for a work piece. The cylindrical grinding device 21 comprises a movable table 22, a grinding wheel 23 arranged to face to a work piece 1 rotatably held above the movable table 22, and a grinding wheel rotationally driving device. The grinding wheel rotationally driving device includes a drive motor 24 and a transmission mechanism for transmitting the turning force of the drive motor 24 through a driving side pulley 25, V-belts 26, and a driven side pulley 27. The driven side pulley 27 is mounted and fixed through a bearing 28 to a rotating shaft of the grinding wheel 23. The components of the grinding wheel rotationally driving device and the bearing 28 are installed on a movable grinding wheel base 29. The movable grinding wheel base 29 is mounted on the fixed base 30 so as to be slidable relative to the fixed base 30 in directions for cutting into and retracting or away from the work piece 1. The movable grinding wheel base 29 is moved by driving of a feed motor 31 provided on the fixed base 30, and the movements of the movable grinding wheel base 29 are effected along parallel guide shafts by rotationally driving a feed shaft 32 connected to the feed motor 31 in normal and reverse directions.

Figure 17:
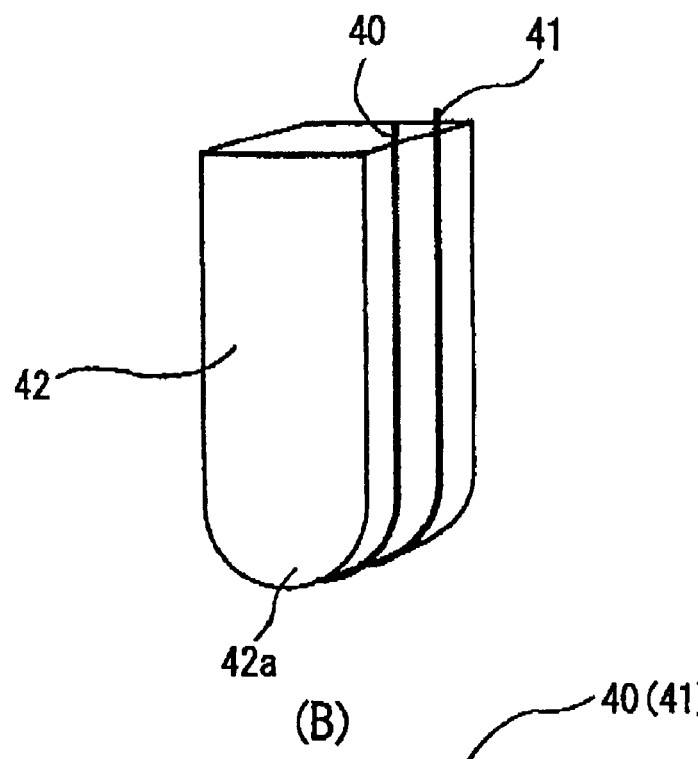
FIG. 17 are a perspective view (A) and a side view (B) illustrating a thermocouple having a holder structure.
Figure 17:
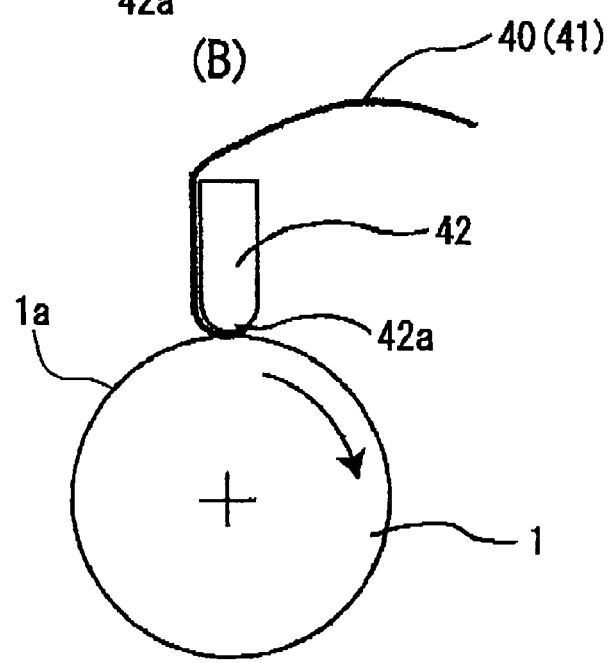

The movable table 22 comprises a pair of movable centers 33 for rotationally supporting both the ends of the work piece 1, bearings 34 and 35 for the respective movable centers 33, and a main spindle motor 36 provided for the bearing 35. The feed motor 31 for controlling depths of cutting of the grinding wheel 23 and the main spindle motor 36 for controlling the rotation of the work piece 1 are controlled by a motor control section 38 of a main control section 37. The main control section 37 includes a microcomputer control section 39 having a CPU, and the motor control section 38 is controlled by the microcomputer control section 39. The surface roughness measuring device (measuring means) comprises a predetermined number of thermocouples 42 constructed by thermocouple wires 40 and 41 (for example, C wires and A wires) and the thermocouples 42 are arranged so as to be in contact with the surface 1*a* to be measured of the work piece 1 at a constant pressure. The thermocouple 42 has a holder construction shown in FIG. 17 in order that the thermocouple wires 40 and 41 of the thermocouple 42 stably abut against the work piece 1 rotating at high speed. Namely, as shown in FIG. 17(A), the thermocouple 42 comprises an insulating block body in the form of a tower head and thermocouple wires 40 and 41 fixed to a forward end curved portion 42*a* of the block in a manner wound thereabout by means of an adhesive or the like. When measuring, parts of the thermocouple wires 40 and 41 positioned at the head of the forward end curved portion 42*a* are pushed to and abut against the surface 1*a* to be measured of the work piece 1 as shown in FIG. 17(B). Moreover, although the thermocouple 42 shown in FIG. 17 has a construction holding the thermocouple wires 40 and 41 along the outer surface of the insulating block body, the thermocouple wires 40 and 41 may be extended through the insulating block body 80 so as to be fixed and held to the block body so that tips of the thermocouple wires 40 and 41 extend from the lower tower head portion 81 of the insulating block body 80 as shown in FIGS. 18(A) and 18(B). The thermocouple wires 40 and 41 abut against the outer circumferential surface 1*a* (the surface to be measured) of the rotating body (work piece) 1.

The thermoelectromotive forces detected by the thermocouple 42 are introduced through a direct current amplifier 43 into the microcomputer control section 39. As in the configurations of embodiment in FIG. 6 and the like, a standard sample (standard work piece) of the work piece 1 is made, and correlation data between thermoelectromotive forces measured on the reference surface of the standard sample and surface roughness have been previously obtained so that such data and inherent values (temperature coefficient α) of the thermocouples are stored in the microcomputer control device. Moreover, the microcomputer control section 39 includes a display section (not shown) for displaying surface roughness measured on the basis of the principle of surface roughness measurement of thermocouple contact type according to the invention. Further, the microcomputer control section 39 also includes processing terminals for outputting measured surface roughness data to other analyzing devices.

With the cylindrical grinding surface roughness measuring device constructed as described above, cylindrical grinding is performed by rotating a work piece 1 above the movable table 22, while adjusting depths of cutting of the grinding wheel 2 by the feed motor 31, during which cylindrical grinding, the thermocouple wires 40 and 41 are pushed against the rotating ground surface 1*a* (surface to be measured) of the work piece 1 at a constant pressure to hold the thermocouple wires in contact with the surface for a predetermined period of time, thereby measuring the thermoelectromotive forces by means of the thermocouple wires 40 and 41. When the measured thermoelectromotive force data have been introduced through the direct current amplifier 43 into the microcomputer control section 39, the microcomputer control section 39 produces surface roughness data from and corresponding to the input measured thermoelectromotive force data on the basis of the previously memorized correlation data between the thermoelectromotive forces and surface roughness and outputs the surface roughness data to the display section for displaying them. Therefore, the in-process surface roughness measurement for the work piece 1 can be carried out, while performing the cylindrical grinding.

Figure 18:
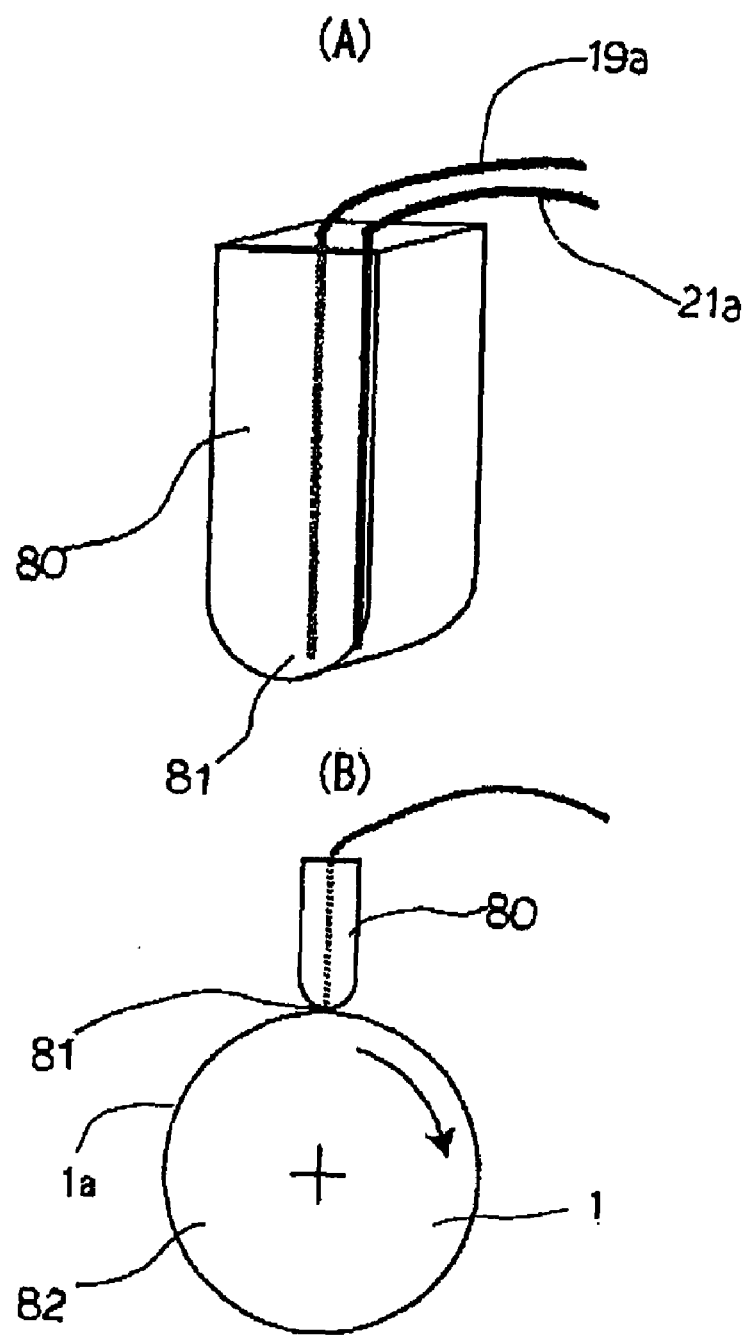
FIG. 18 are a perspective view (A) and a side view (B) illustrating a modification of the thermocouple having a holder structure.
Figure 19:
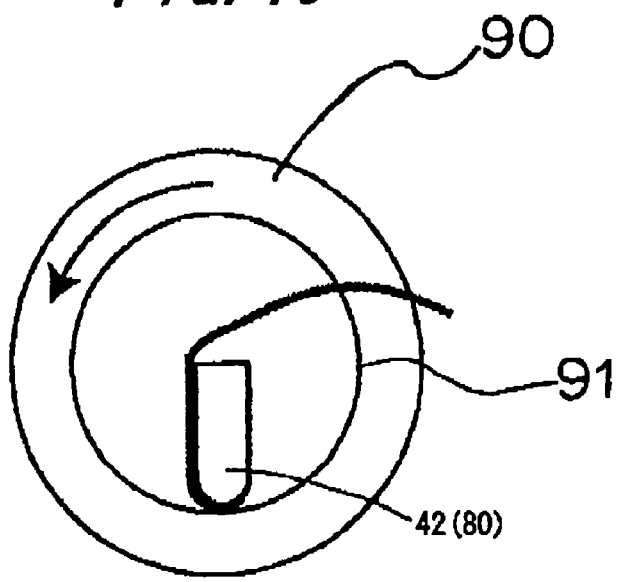
FIG. 19 is a side view illustrating one example of surface state detecting configuration.

While the examples for measuring outer surfaces of circular disk-shaped or cylindrical work pieces are shown in the configurations of the embodiments described above, it will be apparent that the invention is not to be limited to such shapes of work pieces and may be applicable to a wide variety of shapes of work pieces. For example, the in-process surface roughness measurement can be carried out on the hollowed inner surface (surface to be measured) 91 of a hollow cylindrical work piece 90 as shown in FIG. 19 using thermocouples 42 and 80 as shown in FIGS. 17 and 18 inscribing the inner surface 91 of the work piece 90.

Figure 20:
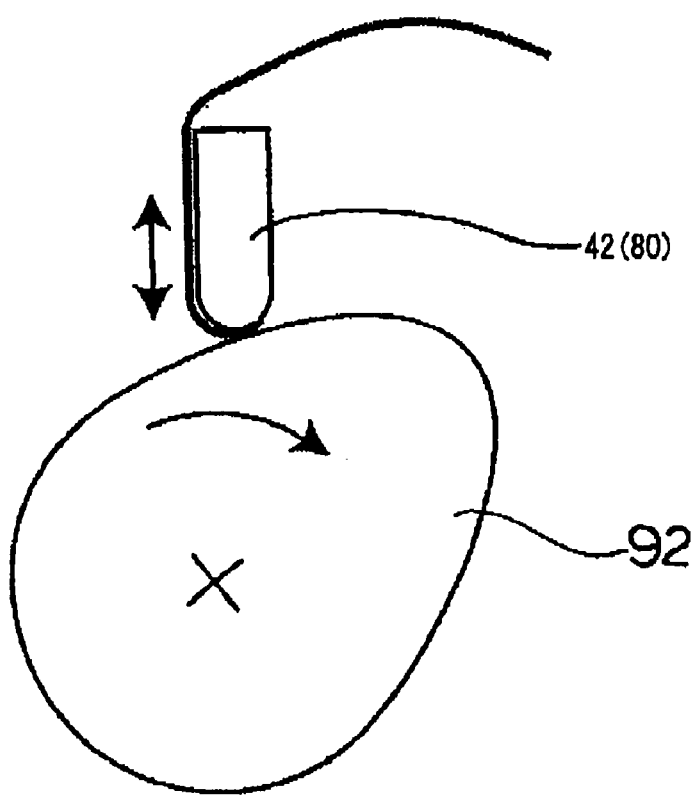
FIG. 20 is a side view illustrating a modification of surface state detecting configuration.

As shown in FIG. 20, moreover, the invention is applicable to a work piece performing an irregular rotation such as a cam motion. In this case, a moving control mechanism (not shown) is provided for moving the thermocouples 42 and 80 as shown in FIGS. 17 and 18 up and down. It is preferable that the thermocouples 42 and 80 are moved upwardly and downwardly in synchronism with the rotation of a work piece 92 by the moving control mechanism in a manner that the thermocouples 42 and 80 abut against the work piece 92 along cam orbits of the work piece 92 at a constant pressure. In the case that surface roughness of such an eccentrically rotating body are measured, if the rotating body is rotated at a constant speed, measuring speed will be varied. It is preferable, therefore, to pursue the surface roughness by an arithmetic operation in consideration of affection of the measuring speeds as shown in FIG. 5.

Figure 21:
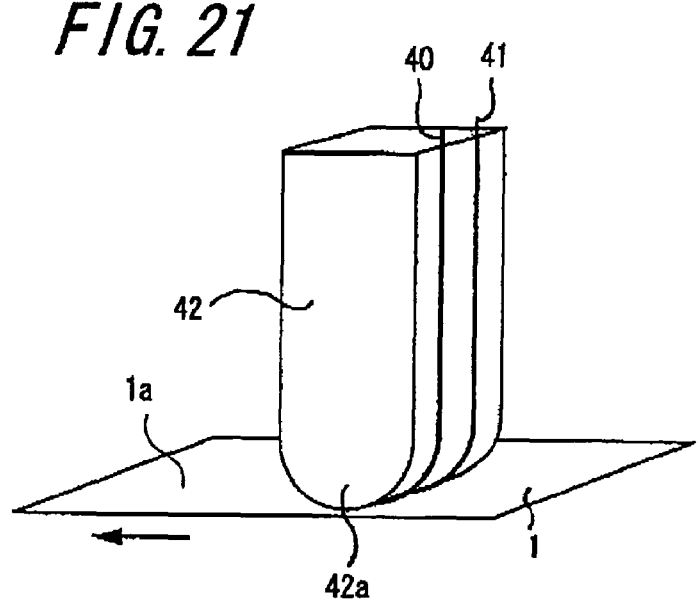
FIG. 21 is a perspective view illustrating the surface state measuring method for an object performing translation motion.
Figure 22:
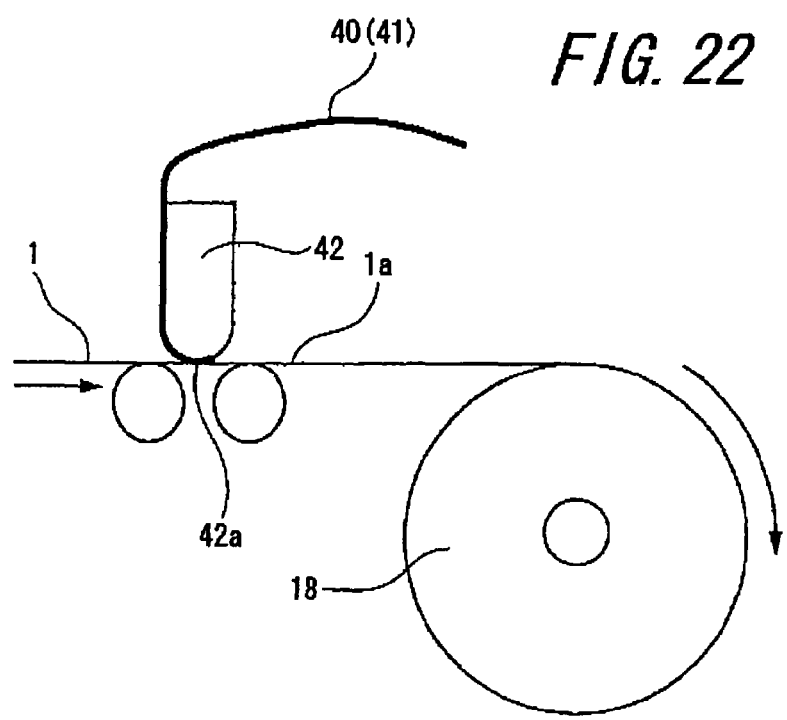
FIG. 22 is a side view illustrating the surface state measuring configuration for an object performing translation motion.

FIG. 21 illustrates a configuration for detecting surface state of a surface 1*a* to be measured in the form of a flat surface of a block-shaped work piece 1 by arranging a thermocouple (for example, the thermocouple 42 as shown in FIG. 17) at a determined position on the moving path (for example, working line) of the work piece which moves in a straight line. Further, FIG. 22 illustrates a configuration for detecting surface state of a rolled surface (surface to be measured) 1*a* of a work piece (rolled steel plate or the like) 1 going to a coil winding-up section 18 for winding up the steel plate into a coil by arranging a thermocouple (for example, thermocouple 42 shown in FIG. 17) at a determined position (for example, a position in the proximity of the coil winding-up section 18) on the moving path (for example, a rolling line).

Figure 23:
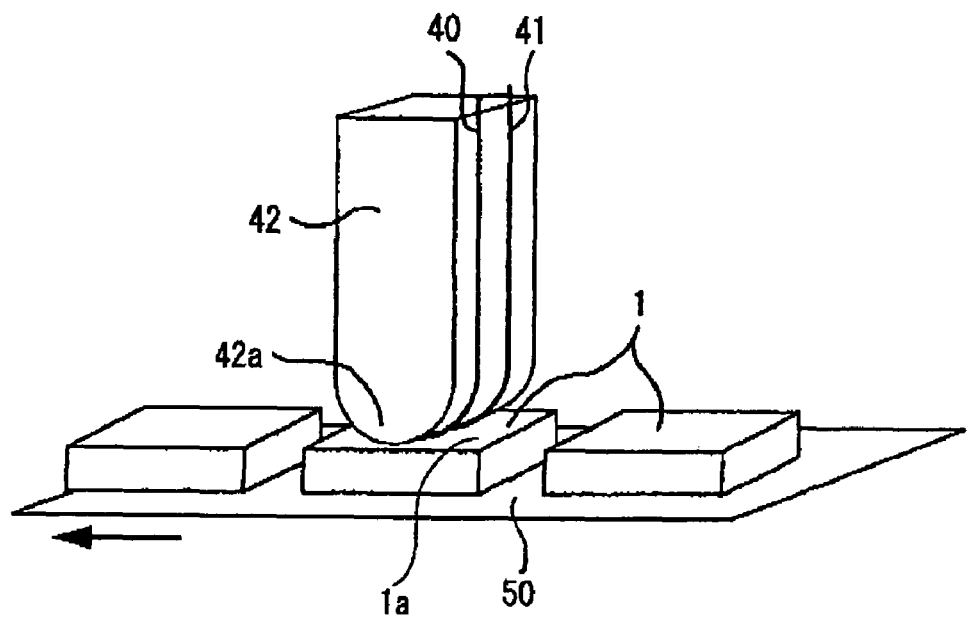
FIG. 23 is a perspective view illustrating the surface state measuring configuration for an object to be measured being transferred.

FIG. 23 illustrates a configuration for detecting surface state of a work piece 1 during its transport. Namely, surface state of the work piece 1 is detected by a thermocouple (for example, thermocouple 42 shown in FIG. 17), while the work piece 1 is being transferred by transfer means 50. The detection can be carried out during surface working or surface treating of the work piece 1 in an in-process manner.

Figure 24:
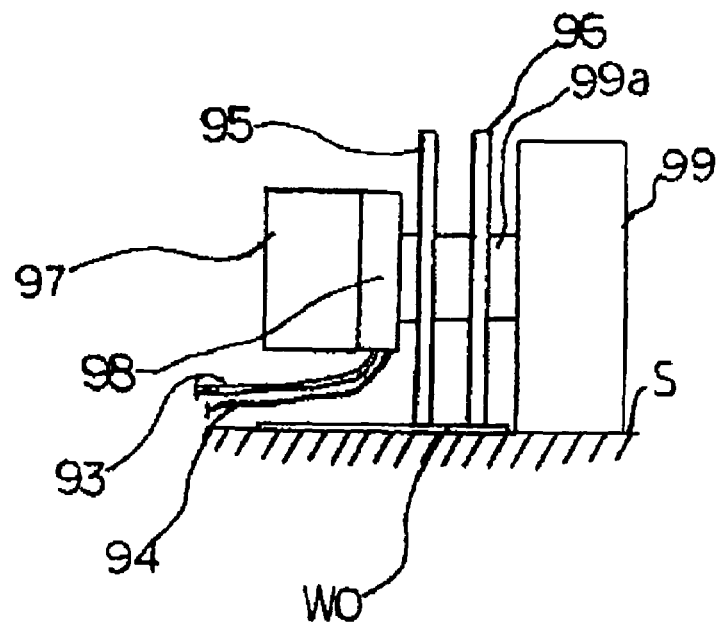
FIG. 24 is a side view illustrating one example of the surface roughness measuring device using a thermocouple comprising rotating probes.

In detecting surface state according to the invention, moreover, a work piece need not be a moving object, and the invention is applicable to a stationary object in contact with a thermocouple moving relative to the object. FIG. 24 illustrates a surface state measuring device for a work piece WO of a conductive material. Respective probes of thermocouples are rotating metal plates 95 and 96 mounted on an output shaft 99a of a drive motor 97. The drive motor 97 may be a stepping motor or the like and its output shaft 99a is supported by a bearing member 99. The bearing member 99 is attached to a base by means of hinges 55 so as to be movable between a forward tilting position and an upright position relative to the work piece WO. The rotating metal plates 95 and 96 are formed from different metals similarly to the CA wire thermocouple and spaced apart from each other. The rotating metal plates 95 and 96 are mounted on the output shaft 99a in a non-electrical continuity state and are connected in an electrical continuity state through a slip ring 98 to CA wires 93 and 94, respectively. When measuring the roughness of the work piece WO, the work piece WO is arranged in a stationary condition on a floor surface S and the bearing member 99 is also arranged on the floor surface S so that the rotating metal plates 95 and 96 as rotating probes are brought into contact with the surface of the work piece WO. The drive motor 97 is then rotationally driven so that the rotating metal plates 95 and 96 are rotated on the surface of the work piece WO. At this time, the rotating metal plates 95 and 96 rotate on their axis so as to scrub the surface of the work piece to generate thermoelectromotive force which is transmitted through the CA wires 93 and 94 to a control section (not shown). Similarly to the configurations of the embodiments described above, surface roughness data can be obtained corresponding to the measured thermoelectromotive forces from the correlation data between the thermoelectromotive forces and surface roughness previously pursued from a standard surface. In the case that the material of the stationary work piece is the same as that of one of thermocouple material, the thermocouple wire of the same material is connected to the work piece and the rotating circular plate made of the other thermocouple material is brought into contact with the surface to be measured so that the rotating circular plate is caused to output through the slip ring in a similar manner to that of FIG. 22, thereby enabling the roughness of the work piece to be measured.

Figure 25:
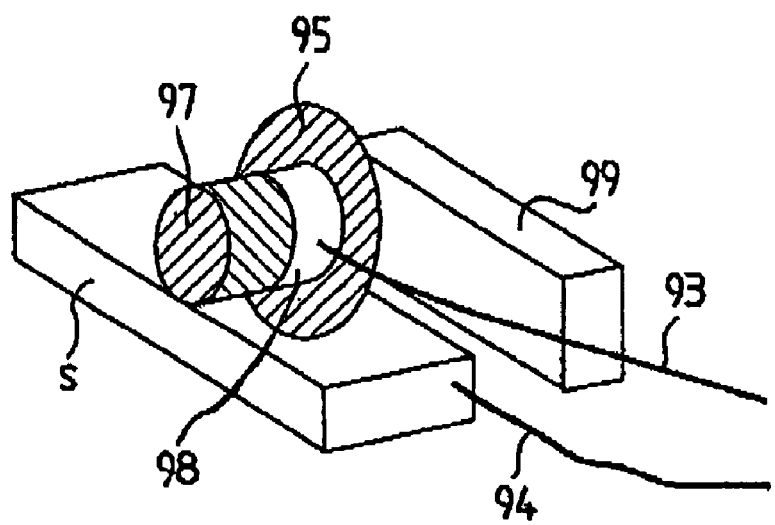
FIG. 25 are a perspective view (A) and a side view (B) illustrating a surface state detecting configuration for three dimensionally scanning by the thermocouple.
Figure 25:
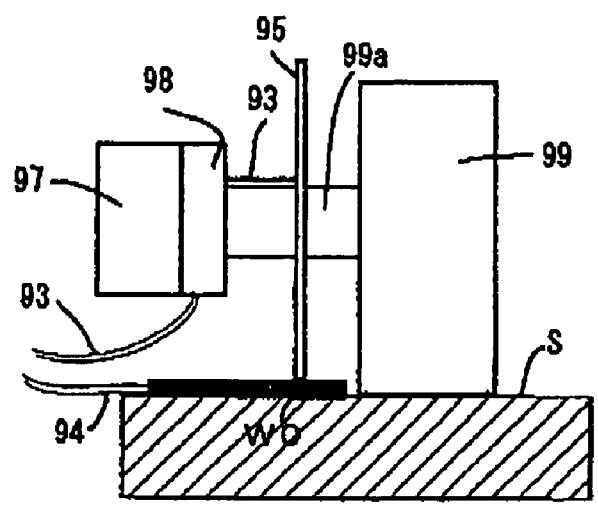

FIG. 25 is a schematic view illustrating modifications of the surface state measuring device shown in FIG. 24. In the modification shown in FIG. 25(A), CA wire 94 is connected to a supporting base S, while in the modification shown in FIG. 25(B), CA wire 94 is connected to a work piece. With such connections, surface condition measurement can be favorably carried out similarly to the case of FIG. 24.

Figure 26:
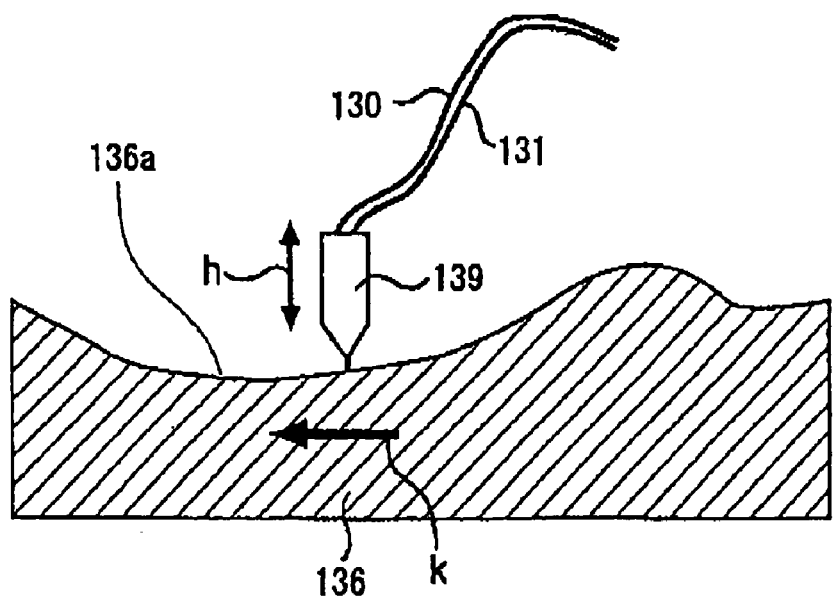
FIG. 26 is a side view illustrating a surface state detecting configuration for an uneven surface to be measured.

FIG. 26 is a schematic view illustrating a method for measuring a surface state by causing a thermocouple 139 to perform three dimensionally scanning. The surface 136a to be measured of an object 136 is scanned by the thermocouple 139 including contact points of thermocouple wires 130 and 131 to measure surface roughness or surface temperatures. In the case that the surface of the object 136 is uneven, that is, having concave and convex portions as shown in FIG. 26, the object to be measured is caused to perform translation motion in the direction shown by an arrow K (or reciprocal translation motion), while said thermocouple 139 is caused to reciprocally move (up and down) in directions shown by an arrow h (direction perpendicular to the moving direction of the surface to be measured), thereby enabling preferable measurement of surface state. The reciprocal movement of the thermocouple 139 as described above can be effected by an automatic control based on the previously obtained information regarding the three dimensional shape of the surface 136a to be measured. Moreover, the operation for the reciprocal movement may be performed so as to cause the distance between the object 136 to be measured and the thermocouple 139 to be constant while monitoring the distance by means of distance measuring means provided on the surface state measuring device.

Figure 27:
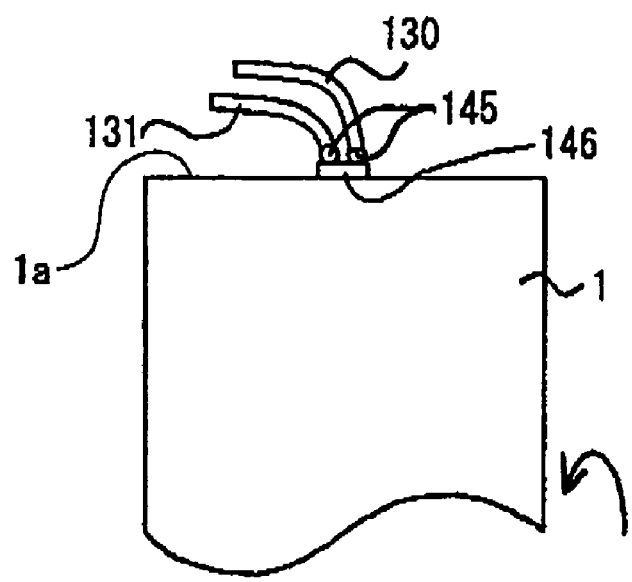
FIG. 27 is a front elevation illustrating a thermocouple having a small piece of a wear resistant material attached to tips of thermocouple wires.
Figure 27:
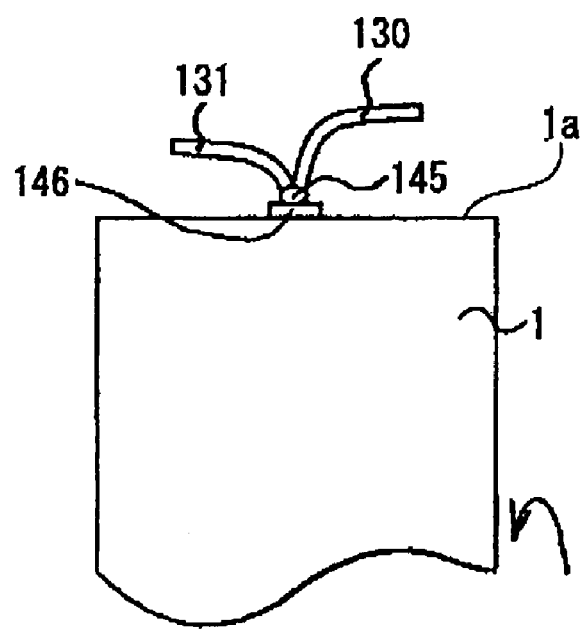

FIG. 27 is a schematic view illustrating a surface state measuring device having a very small piece 146 of a wear resistant material fixed to tips of the thermocouple wires 130 and 131. As shown in FIG. 27(A), the tips 145 of the thermocouple wires 130 and 131 forming respective probes are spaced apart from each other, and the very small wear resistant piece 146 is fixed to the tips. When the tips of the thermocouple wires 130 and 131 are brought into contact with the surface 1a to be measured of a work piece 1 rotating in the direction shown by an arrow, the wear resistance of the thermocouple wires is remarkably improved with the aid of the very small piece 146. FIG. 27(B) illustrates a case that tips 145 of thermocouple wires 130 and 131 are combined with each other. Similarly to the case of the spaced tips as shown in FIG. 27(A), the durability of the thermocouple consisting of the thermocouple wires 130 and 131 is remarkably improved with the aid of the small piece.

INDUSTRIAL APPLICABLE FIELD

The surface state detecting method and device according to the invention are applicable to a wide variety of measuring objects (work pieces), particularly to all the electrically conductive materials, and capable of measuring the states of surfaces in an in-process manner without being affected by external disturbances even under any dynamic conditions, and can achieve a simplification of measuring system. By performing the in-process measurement of surface roughness, since it becomes possible to monitor the accuracy of ground surfaces during grinding machining by the machine tools, increase of unmanned machine tools and smooth automatic operations without troubles can be progressed so that the improvement in production efficiency and product quality can be realized.

Even with fine portions or narrow portions which would probably require particular processes such as cutting and the like to expose the surface to be measured for measuring their surface roughness by the stylus type or optical type methods or drives of the prior art, according to the surface state measuring method and device of the invention, the surface state can directly measured without requiring cutting or any other process, and the surface quality of the work piece being mounted on the machine even in a post-process measurement can also be rapidly estimated so that the improvement in production efficiency and production quality can be realized.

The invention claimed is:

1. A method for detecting surface state of a work piece wherein:
   first and second measuring thermocouples in contact with a surface to be measured of the work piece are caused to perform movements with relation to the surface to be measured so that generated thermoelectromotive forces of the measuring thermocouples are measured, and
   a surface roughness, of the surface to be measured $Ry = (\alpha 2 \cdot \Delta E1 - \alpha 1 \cdot \Delta E2)/(\alpha 2 \cdot \beta 1 - \alpha 1 \cdot \beta 2)$ and/or a surface temperature variation of the surface to be measured $\Delta T = \beta 2 \cdot \Delta E1 - \beta 1 \cdot \Delta E2)/(\alpha 1 \cdot \beta 2 - \alpha 2 \cdot \beta 1)$, is obtained from the measured thermoelectromotive force on the basis of first correlation data $\Delta E = \alpha 1 \cdot \Delta T + \beta 1 Ry$ and second correlation data $\alpha E = \alpha 2 \cdot \Delta T + \beta 2 \cdot Ry$ between thermoelectromotive forces, surface roughness and/or surface temperature variations;

where:
- ΔE is the thermoelectromotive force, ΔT is the surface temperature variation,
- Ry is the surface roughness, α1 is an inherent temperature coefficient of the first measuring thermocouple and the first data collecting thermocouple, α2 is an inherent temperature coefficient of the second measuring thermocouple and the second data collecting thermocouple,
- β1 is a roughness coefficient induced from the relation between the thermoelectromotive force and the surface roughness depending on the contact condition and the relative movement condition of the first measuring thermocouple and the first data collecting thermocouple,
- β2 is a roughness coefficient induced from the relation between the thermolectromotive force and the surface roughness depending on the contact condition and the relative movement condition of the second measuring thermocouple and the second data collecting thermocouple, and
- the surface roughness and/or surface temperature variations are previously obtained by bringing first and second data collecting thermocouples, respectively, the same as or the same kind as the first and second measuring thermocouples, respectively, into contact with a standard surface whose surface roughness and/or surface temperature has been known and by causing the data collecting thermocouples to perform a relative movement with respect to the standard surface under the same contact condition and the same relative movement conditions as those of the first and second measuring thermocouples with respect to the surface to be measured.

2. The method for detecting surface state of a work piece as claimed in claim 1, wherein the measuring thermocouple is caused to perform the relative movement under a contact condition producing a relative speed at the contact point with the surface to be measured.

3. The method for detecting surface state of a work piece as claimed in claim 2, wherein in the case of the surface to be measured having an electric conductivity, the thermoelectromotive force is measured by bringing tips of first and second thermocouple wires constituting the measuring thermocouple into contact with the surface to be measured under a condition that the tips are spaced apart from each other.

4. The method for detecting surface state of a work piece as claimed in claim 2, wherein the tips of the first and second thermocouple wires are connected by a wear resistant member and the thermoelectromotive force is measured by bringing the wear resistant member into contact with the surface to be measured.

5. The method for detecting surface state of a work piece as claimed in claim 2, wherein in the case of the entire work piece including the surface to be measured integrally formed from an electrically conductive material, the thermoelectromotive force is measured by bringing the tip of one of the first and second thermocouple wires constituting the measuring thermocouple into contact with the surface to be measured and connecting the tip of the other thermocouple wire to part of the work piece other than its surface to be measured.

6. The method for detecting surface state of a work piece as claimed in claim 1, wherein surface roughness and/or surface temperature variations at a plurality of locations of the surface to be measured are obtained at a time, by bringing a plurality of sets of measuring thermocouples into contact with the surface to be measured at the plurality of locations, each set consisting of the first and second measuring thermocouples.

7. The method for detecting surface state of a work piece as claimed in claim 1, wherein the first and second measuring thermocouple are of different kinds.

8. The method for detecting surface state of a work piece as claimed in claim 7, wherein the first and second measuring thermocouples are brought into contact with the surface to be measured under a relative movement condition that relative speeds of the first and second measuring thermocouples relative to the surface to be measured at contact points therewith are equal to each other.

9. The method for detecting surface state of a work piece as claimed in claim 7, wherein the first and second measuring thermocouples are brought into contact with the surface to be measured under relative movement conditions that relative speeds of the first and second measuring thermocouples with respect to the surface to be measured at contact points therewith are different from each other.

10. The method for detecting surface state of a work piece as claimed in claim 1, wherein the first and second measuring thermocouple are of the same kind.

11. The method for detecting surface state of a work piece as claimed in claim 1, wherein one of the first and second measuring thermocouples is brought into contact with the surface to be measured under a relative movement condition that the relative speed of the one of the first and second measuring thermocouples with respect to the surface to be measured at the contact point therewith is zero.

12. The method for detecting surface state of a work piece as claimed in claim 1, wherein the surface to be measured is a two or three dimensional curved surface.

13. The method for detecting surface state of a work piece as claimed in claim 12, wherein the surface to be measured is a surface of rotation.

14. The method for detecting surface state of a work piece as claimed in claim 12, wherein the case that the work piece performs rotating movement or linear movement, the measuring thermocouple is brought into contact with the surface to be measured at a constant pressure at a determined position on a moving path of the surface to be measured.

15. The method for detecting surface state of a work piece as claimed in claim 14, wherein the case that the contact point between the measuring thermocouple and the surface to be measured is displaced in a direction crossing the direction of the relative movement, contact pressure between the measuring thermocouple and the surface to be measured is kept constant by enabling reciprocal movement of the measuring thermocouple in the crossing direction.

16. The method for detecting surface state of a work piece as claimed in claim 12, wherein the case that the work piece is under a stationary condition, the measuring thermocouple is adapted to move on the surface to be measured under a condition contacting the work piece at a constant pressure.

17. The method for detecting surface state of a work piece as claimed in claim 1, wherein the surface to be measured is a flat surface.

18. The method for detecting surface state of a work piece as claimed in claim 1, wherein the surface to be measured is an irregular surface.

19. The method for detecting surface state of a work piece as claimed in claim 1, wherein the work piece has been worked or processed with its surface, and the surface to be measured is the worked or processed surface.

20. The method for detecting surface state of a work piece as claimed in claim 19, wherein the measurement of the thermoelectromotive force by the measuring thermocouple is performed simultaneously with the surface working or surface processing of the work piece.

21. A method for detecting surface state of a work piece, wherein first and second data collecting thermocouples in contact with a standard surface whose surface roughness and surface temperature have been known are caused to perform movements with relation to the standard surface to generate thermoelectromotive force of the data collecting thermocouples so that first correlation data $\Delta E=\alpha 1 \cdot \Delta T+\beta 1 \cdot Ry$ and second correlation data $\Delta E=\alpha 2 \cdot \Delta T+\beta 2 \cdot Ry$;

where:

$\Delta E$ is the thermoelectromotive force, $\Delta T$ is the surface temperature variation, Ry is the surface roughness, $\alpha 1$ is an inherent temperature coefficient of the first measuring thermocouple and the first data collecting thermocouple, $\alpha 2$ is an inherent temperature coefficient of the second measuring thermocouple and the second data collecting thermocouple, $\beta 1$ is a roughness coefficient induced from the relation between the thermoelectromotive force and the surface roughness depending on the contact condition and the relative movement condition of the first measuring thermocouple and the first data collecting thermocouple, and $\beta 2$ is a roughness coefficient induced from the relation between the thermoelectromotive force and the surface roughness depending on the contact condition and the relative movement condition of the second measuring thermocouple and the second data collecting thermocouple, the generated thermoelectromotive forces of the data collecting thermocouples and the surface roughness are previously obtained with surface temperature as a parameter, and the surface temperature of a surface to be measured of the work piece is measured, and that first and second measuring thermocouples the same as or the same kind as the first and second data collecting thermocouples, respectively, are brought into contact with the surface to be measured and are caused to perform relative movements with respect to the surface to be measured under the same contact conditions and the same relative movement conditions as those of the data collecting thermocouples with respect to the standard surface so as to generate thermoelectromotive forces of the thermocouples and the generated thermoelectromotive forces are measured, from which measured thermoelectromotive forces, surface roughness of the surface to be measured $Ry=(\alpha 2 \cdot \Delta E1-\alpha 1 \cdot \Delta E2)/(\alpha 2 \cdot \beta 1-\alpha 1 \cdot \beta 2)$ is obtained on the basis of the correlation data corresponding to the measured surface temperature.

22. The method for detecting surface state of a work piece as claimed in claim 21, wherein the measuring thermocouple is caused to perform the relative movement under a contact condition producing a relative speed at the contact point with the surface to be measured.

23. The method for detecting surface state of a work piece as claimed in claim 21, wherein surface roughness and/or surface temperature variations at a plurality of locations of the surface to be measured are obtained at a time, by bringing a plurality sets of measuring thermocouples into contact with the surface to be measured at the plurality of locations, each set consisting of the first and second measuring thermocouples.

24. The method for detecting surface state of a work piece as claimed in claim 21, wherein the first and second measuring thermocouple are of different kinds.

25. The method for detecting surface state of a work piece as claimed in claim 21, wherein the first and second measuring thermocouple are of the same kind.

26. The method for detecting surface state of a work piece as claimed in claim 21, wherein one of the first and second measuring thermocouples is brought into contact with the surface to be measured under a relative movement condition that the relative speed of the one of the first and second measuring thermocouples with respect to the surface to be measured at the contact point therewith is zero.

27. A device for detecting surface state of a work piece wherein comprising:

measuring means for measuring thermoelectromotive force of a measuring thermocouple generated by causing the measuring thermocouple to perform a movements with relation to a surface to be measured of the work piece under a condition contacting the surface to be measured;

a memory section for memorizing correlation data between thermoelectromotive forces, surface roughness and/or surface temperature variations previously obtained by bringing a data collecting thermocouple the same as or the same kind as the measuring thermocouple into contact with a standard surface whose surface roughness and/or surface temperature has been known and causing the data collecting thermocouple to perform a relative movement with respect to the standard surface under the same contact condition and the same relative movement condition as those of the measuring thermocouple with respect to the surface to be measured;

an arithmetic section for calculating surface roughness and/or surface temperature variation of the surface to be measured from the thermoelectromotive force measured by the measuring means on the basis of the correlation data; and an information output section for outputting information regarding the surface roughness and/or surface temperature variation of the surface to be measured calculated by the arithmetic section, wherein, the measuring means is constructed to separately measure the thermoelectromotive force $\Delta E1$ generated by a first measuring thermocouple and the thermoelectromotive force $\Delta E2$ generated by a second measuring thermocouple, the memory section is constructed to memorize first correlation data $\Delta E=\alpha 1 \cdot \Delta T+\beta 1 \cdot Ry$ obtained by the use of a first data collecting thermocouple the same as or the same kind as the first measuring thermocouple and second correlation data $\Delta E=\alpha 2 \cdot \Delta T+\beta 2 \cdot Ry$ obtained by the use of a second data collecting thermocouple the same as or the same kind as the second measuring thermocouple, and the arithmetic section is constructed to calculate the surface roughness of the surface to be measured $Ry=(\alpha 2 \cdot \Delta E1-\alpha 1 \cdot \Delta E2)/(\alpha 2 \cdot \beta 1-\alpha 1 \cdot \beta 2)$ and/or surface temperature variation $\Delta T=(\beta 2 \cdot \Delta E1-\beta 1 \cdot \Delta E2)/(\alpha 1 \cdot \beta 2-\alpha 2 \cdot \beta 1)$ on the basis of the first and second correlation data, where $\alpha 1$ is an inherent temperature coefficient of the first measuring thermocouple and the first data collecting thermocouple, $\alpha 2$ is an inherent temperature coefficient of the second measuring thermocouple and the second data collecting thermocouple, $\beta 1$ is a roughness coefficient induced from the relation between the thermoelectromotive force and the surface roughness depending on the contact condition and the relative movement condition of the first measuring thermocouple and the first data collecting thermocouple, and $\beta 2$ is a roughness coefficient induced from the relation between the thermoelectromotive force and the surface roughness depending on the contact condition and the relative movement condition of the second measuring thermocouple and the second data collecting thermocouple.

28. The device for detecting surface state of a work piece as claimed in claim 27, wherein the first and second measuring thermocouples are of the same kind having the same temperature coefficient α1, and the arithmetic section is adapted to calculate the surface roughness of the surface to be measured Ry=(ΔE1−ΔE2)/(β1−β2) and/or the surface temperature variation ΔT=(β2·ΔE1−β1·ΔE2)/ (α1·β2−α1·β1).

29. The device for detecting surface state of a work piece, as claimed in claim 27, wherein
the measuring means is constructed to measure the thermoelectromotive force ΔE1 by causing the first measuring thermocouple to perform a relative movement with respect to the surface to be measured under a contact condition producing a relative speed at the contact point of the first measuring thermocouple with the surface to be measured and to measure the thermoelectromotive force ΔE2 by causing the second measuring thermocouple to perform a relative movement with respect to the surface to be measured under a contact condition not producing relative speed at the contact point of the second measuring thermocouple with the surface to be measured, and
the memory section is constructed to memorize the first correlation data ΔE=α1·ΔT+β1·Ry obtained using the first data collecting thermocouple and the second correlation data ΔE=α2ΔT obtained using the second data collecting thermocouple, and that the arithmetic section is constructed to calculate the surface roughness of the surface to be measured Ry=(α2·ΔE1−α1·ΔE2)/(α2·β1) and/or surface temperature variation ΔT=ΔE2/ α2 from ΔE1=α1·ΔT+β1·Ry and ΔE2=α2·ΔT.

30. The device for detecting surface state of a work piece as claimed in claim 29, wherein the first and second measuring thermocouples are of the same kind, and the arithmetic section is constructed to calculate the surface roughness of the surface to be measured Ry=(ΔE1−ΔE2)/(β1−β2).

31. The device for detecting surface state of a work piece as claimed in claim 27, wherein the case that the surface temperature of the surface to be measured is constant and the surface temperature variation ΔT is zero or already known, the surface roughness of the surface to be measured is detected using only one measuring thermocouple.

32. The device for detecting surface state of a work piece as claimed in claim 27, wherein the case that the surface to be measured has an electric conductivity, the measuring means is so constructed that the thermoelectromotive force is measured by bringing tips of first and second thermocouple wires constituting the measuring thermocouple into contact with the surface to be measured under a condition that the tips are spaced apart from each other.

33. The device for detecting surface state of a work piece as claimed in claim 27, wherein the measuring means is constructed to measure the thermoelectromotive force by bringing a wear resistant member connecting the tips of the first and second thermocouple wires to each other into contact with the surface to be measured.

34. The device for detecting surface state of a work piece as claimed in claim 27, wherein the case that the entire work piece including the surface to be measured is integrally formed from an electrically conductive material, the measuring means is constructed to measure the thermoelectromotive force by bringing the tip of one of the first and second thermocouple wires constituting the measuring thermocouple into contact with the surface to be measured and connecting the tip of the other thermocouple wire to part of the work piece other than the surface to be measured.

35. The device for detecting surface state of a work piece as claimed in claim 27, wherein the tip of at least one of the first and second thermocouple wires constituting the measuring thermocouple is constructed by a rotatable circular disk-shaped probe adapted to be in point contact with the surface to be measured.

36. The device for detecting surface state of a work piece as claimed in claim 35, wherein the measuring means is so constructed to have the circular disk-shaped probe adapted to be forcedly rotated so as to produce a relative speed at a contact point with the surface to be measured.

37. The device for detecting surface state of a work piece as claimed in claim 35, wherein the measuring means is so constructed to have a circular disk-shaped probe adapted to perform a free rotation so as not to produce any relative speed at a contact point with the surface to be measured.

38. The device for detecting surface state of a work piece as claimed in claim 27, wherein the tip of at least one of the first and second thermocouple wires constituting the measuring thermocouple is constructed as a probe so that the thermocouple wire itself comes into contact with the surface to be measured.

39. The device for detecting surface state of a work piece as claimed in claim 27, wherein the tip of at least one of the first and second thermocouple wires constituting the measuring thermocouple is constructed to be able to perform reciprocal movements in directions crossing the direction of relative movement with respect to the surface to be measured so as to keep a contact pressure constant with the surface to be measured.

40. The device for detecting a surface state of a work piece as claimed in claim 27, wherein the case that the measuring means comprises at least one set of the first and second measuring thermocouples, a common thermocouple wire is used both as one of the first and second thermocouple wires constituting the first measuring thermocouple and one of the first and second thermocouple wires constituting the second measuring thermocouple.

41. The device for detecting a surface state of a work piece as claimed in claim 27, wherein the case that the work piece has been subjected to surface working or surface processing and the surface to be measured is one which has been subjected to the surface working or surface processing, the measuring means is arranged on the line of the surface working or surface processing.

* * * * *